(12) United States Patent
Peukert et al.

(10) Patent No.: US 7,863,280 B2
(45) Date of Patent: Jan. 4, 2011

(54) SUBSTITUTED 2-PYRIDONE DERIVATIVES, METHOD FOR THEIR PREPARATION AND THEIR USE AS MEDICAMENT

(75) Inventors: Stefan Peukert, Arlington, MA (US); Stefan Guessregen, Wiesbaden (DE); Armin Hofmeister, Dexheim (DE); Herman Schreuder, Hofheim (DE); Uwe Schwahn, Sulzbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 876 days.

(21) Appl. No.: 11/733,833

(22) Filed: Apr. 11, 2007

(65) Prior Publication Data
US 2007/0281948 A1    Dec. 6, 2007

Related U.S. Application Data

(63) Continuation of application No. PCT/EP2005/010697, filed on Oct. 5, 2005.

(30) Foreign Application Priority Data

Oct. 15, 2004    (DE)    ............... 10 2004 050 196

(51) Int. Cl.
  *C07D 401/02* (2006.01)
  *A61K 31/44* (2006.01)

(52) U.S. Cl. ............... 514/256; 514/277; 514/340; 514/345; 544/333; 546/255; 546/256; 546/261

(58) Field of Classification Search ............... None
See application file for complete search history.

(56) References Cited

U.S. PATENT DOCUMENTS
2005/0080096 A1    4/2005    Ishida et al.

FOREIGN PATENT DOCUMENTS
EP           0109628      5/1984
WO     WO 93/07137      4/1993

*Primary Examiner*—Zinna N Davis
(74) *Attorney, Agent, or Firm*—Serena Farquharson-Torres

(57) ABSTRACT

This invention relates to compounds of formula (I),

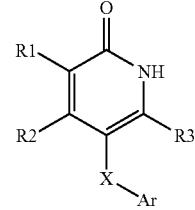

(I)

wherein R1 and R3 independently represent fluorine, methoxy, —$OCF_3$, $C_2$-$C_3$-alkenyl or $C_1$-$C_4$-alkyl which is optionally substituted by chlorine, methoxy or one, two or three fluorine atoms; R2 represents hydrogen, fluorine, methoxy, —$OCF_3$, $C_2$-$C_3$-alkenyl or $C_1$-$C_4$-alkyl which is optionally substituted by chlorine, methoxy or one, two or three fluorine atoms; X represents O, S, NH or N($C_1$-$C_3$-alkyl); and Ar represents an unsubstituted or at least monosubstituted aryl or heteroaryl. Said compounds are inhibitors of poly(ADP-ribose) polymerase (PARP), and may be used for the treatment of a variety of disorders.

8 Claims, No Drawings

SUBSTITUTED 2-PYRIDONE DERIVATIVES, METHOD FOR THEIR PREPARATION AND THEIR USE AS MEDICAMENT

This application is a CON of PCT/EP05/10697 filed Oct. 5, 2005.

FIELD OF THE INVENTION

This invention relates to substituted 2-pyridone derivatives, method for their preparation and their use as medicament, and particularly to 3,6-substituted 5-arylamino-1h-pyridine-2-one derivatives and related compounds as poly(ADP-ribose) polymerase (PARP) inhibitors in the treatment of tissue damage or disease caused by necrosis or apoptosis The invention relates to compounds of the general formula (I)

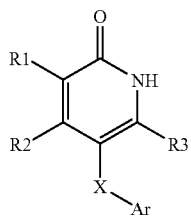

where the definitions of the substituents R1, R2, R3, Ar and X are stated in the following text, and to the physiologically tolerated salts thereof, method for the preparation of these compounds and their use as PARP inhibitors.

BACKGROUND OF THE INVENTION

Poly(adenosine 5'-diphosphate-ribose)polymerase [poly(ADP-ribose) polymerase, PARP], which is also known as poly(ADP-ribose) synthetase (PARS), is a chromatin-bound nuclear enzyme of eukaryotic cells, of which approximately $2 \times 10^5$ molecules are present per nucleus. PARP is, according to the most recent research results, involved in the pathogenesis of various disorders, and thus inhibition of PARP enzyme activity may have beneficial effects on the course of disorders in preclinical animal models (Cristina Cosi, Expert Opin. Ther. Patents, 2002, 12, 1047-1071 and L. Virag and C. Szabo, Pharmacol. Rev., 2002, 54, 1-54). Poly(ADP-ribose) polymerase occurs in all eukaryotic organisms with the exception of yeast, and is part of the genome surveillance network to protect the genetic information from genotoxic influences. DNA damage induces the enzymatic activity of poly(ADP-ribose) polymerase, leading under physiological conditions to repair of the errors recognized by the enzyme in the DNA. However, in pathological situations, poly(ADP-ribose) polymerase may be strongly activated by free-radical oxygen species—as is the case in ischemia, hypoxia, reperfusion or in inflammatory processes—resulting in consumption by the enzyme of large amounts of its substrate NAD. This depletion of NAD is one of the reasons for the death of cells to be observed in the affected tissue (the so-called energy crisis theory). The therapeutic use of PARP inhibitors is in the prevention or reduction of this NAD depletion in tissue. Apart from the role, described herein, in signal transmission ranging from oxidative stress in cells to NAD depletion, further cellular functions of PARP are suggested in the current literature, and these might likewise play a role in the molecular mechanism of action of PARP inhibitors in pathological situations (A. Chiarugi, Trends Pharmacol. Sci., 2002, 23, 122-129). Irrespective of this unresolved discussion about the molecular mechanism of action, the therapeutic efficacy of various PARP inhibitors has been shown in several preclinical animal models: thus, for example, for acute myocardial infarction, acute renal failure, cerebral ischemia (stroke), neurodegenerative disorders (e.g. a model of Parkinson's disease), diabetes, xenobiotic-induced hepatotoxicity, arthritis, shock lung, septic shock and as sensitizer in the chemotherapy of neoplastic disorders (summarized in L. Virag and C. Szabo, Pharmacol. Rev., 2002, 54, 1-54).

It has specifically been possible to show that PARP inhibitors bring about morphological and functional improvements not only in acute myocardial infarction (J. Bowes et al., Eur. J. Pharmacol., 1998, 359, 143-150; L. Liaudet et al., Br. J. Pharmacol., 2001, 133, 1424-1430; N. Wayman et al., Eur. J. Pharmacol., 2001, 430, 93-100), but also significantly better cardiac functions have been measured in chronic heart failure during PARP inhibitor treatment (P. Pacher, J. Am. Coll. Cardiol., 2002, 40, 1006-1016). The hypoperfusion like that which, in the infarcted heart, brings about losses of function of the organ through death of cells also appears in stroke at the start of the chain of events which leads to losses or complete failure of individual regions, and thus functions, of the organ. Accordingly, it has been possible to show the efficacy of PARP inhibitors—besides the genetic ablation of the PARP-1 gene (M. J. L. Eliasson et al., Nat. Med., 1997, 10, 1089-1095)—also in models of cerebral ischemia (K. Takahashi et al., L. Cereb. Blood Flow Metab., 1997, 11, 1137-1142), of MPTP-induced neurotoxicity (C. Cosi et al., Brain Res., 1996, 729, 264-269) and of neuronal excitotoxicity (A. S. Mandir et al., J. Neurosci., 2000, 21, 8005-8011). A further finding which is very important in connection with cardiovascular disorders is the efficacy of PARP inhibition in the ischemically damaged kidney, where improvements in the filtration function of the organ have likewise been found in animals treated with PARP inhibitors compared with those treated with placebo (D. R. Martin et al., Am. J. Physiol. Regulatory Integrative Comp. Physiol., 2000, 279, R1834-R1840). In contrast to the acute ischemic insults of the above-mentioned disorders, chronic PARP activation occurs in various pathologies such as, for example, in diabetes. The efficacy of PARP inhibitors has been demonstrated both in preclinical models of type I diabetes (W. L. Suarez-Pinzon et al., Diabetes, 2003, 52, 1683-1688) and in those of type II diabetes (F. G. Soriano et al., Nat. Med., 2001, 7, 108-113; F. G. Soriano et al., Circulation, 2001, 89, 684-691). The beneficial effect of PARP inhibitors in type I diabetes is attributable to their antiinflammatory properties, which it has also been possible to show in further preclinical models, such as of chronic colitis (H. B. Jijon et al., Am. J. Physiol. Gastrointest. Liver Physiol., 2000, 279, G641-G651), of collagen-induced arthritis (H. Kröger et al., Inflammation, 1996, 20, 203-215) and in septic shock (B. Zingarelli et al., Shock, 1996, 5, 258-264). In addition, PARP inhibitors have a sensitizing effect on tumors in chemotherapy on mice (L. Tentori et al., Blood, 2002, 99, 2241-2244).

It has been disclosed in the literature (for example C. Cosi, Expert Opin. Ther. patents, 2002, 12, 1047-1071; Southan et al., Current Medicinal Chemistry, 2003, 10, 321-340) that many different classes of chemical compounds can be used as PARP inhibitors, such as, for example, derivatives of indoles, benzimidazoles, isoquinolinols or quinazolinones. Many of the previously disclosed PARP inhibitors are derivatives of a bi- or polycyclic basic structure. Pyridone derivatives and their possible use as pharmaceutically active substances are known. The use of pyridone derivatives as PARP inhibitors has, however, not yet been described. The pyridone derivatives described in the literature have a different substitution pattern by comparison with the compounds of the invention of the formula I.

U.S. Pat. No. 4,431,651 describes 2-pyridone derivatives as cardiotonics which have a substituted phenyl or pyridinyl radical at position 5.

U.S. Pat. No. 4,699,914 describes 2-pyridone derivatives for the treatment of congestive heart failure which have an imidazolylthienyl or an imidazolylphenyl group at position 5.

EP-A 489327 describes chroman derivatives which show an effect on the cardiovascular system and may be substituted by a 2-pyridone-amino radical.

WO93/07137 describes pyridinol derivatives as protein kinase agonists which have various substituents at position 3.

WO95/00511 describes naphthyridine and pyridopyrazone derivatives having antirheumatic properties which may be substituted by a 2-pyridone-amino radical.

WO95/13272 describes chroman derivative for the treatment of cardiovascular disorders which may be substituted by a dihydroxopyridyl radical.

WO01/02400 describes phenyl, pyridinyl and pyrimidinyl derivatives which, besides a halogen and an amino group, have an unsubstituted or monosubstituted 2-pyridine-amino radical and serve as intermediates for preparing fused imidazole derivatives which can be used as adenosine A2 receptor antagonists.

WO01/25220 and US 2004/0116388 describe triazine derivatives as kinase inhibitors which may have a 2-pyridoneamino radical.

SUMMARY OF THE INVENTION

Since diseases, such as myocardial infarction, which can be treated by inhibition of PARP represents a serious risk for the health of humans and other mammals, there is a great need for novel pharmaceuticals which have an advantageous therapeutic profile for the treatment of such diseases. The present invention is therefore based on the object of providing novel compounds which have an inhibitory effect on PARP.

The present invention relates to substituted 2-pyridone derivatives of the formula (I)

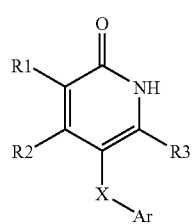

(I)

in which the meanings are:

R1 and R3 independently of one another
    fluorine, methoxy, —$OCF_3$, $C_2$-$C_3$-alkenyl or $C_1$-$C_4$-alkyl which is optionally substituted by chlorine, methoxy or one, two or three fluorine atoms;

R2 hydrogen, fluorine, methoxy, —$OCF_3$, $C_2$-$C_3$-alkenyl or $C_1$-$C_4$-alkyl which is optionally substituted by chlorine, methoxy or one, two or three fluorine atoms;

X O, S, NH or N($C_1$-$C_3$-alkyl);

Ar unsubstituted or at least monosubstituted aryl or heteroaryl, where the substituents are selected from the group consisting of:
    fluorine, chlorine, bromine, —$CF_3$, —$OCF_3$, —$NO_2$, —CN, —C(O)($C_1$-$C_6$-alkyl), $NH_2$, —NHC(O)($C_1$-$C_6$-alkyl), hydroxy, oxo, $C_1$-$C_6$-alkyl, $C_1$-$C_6$-alkoxy, —NH($C_1$-$C_6$-alkyl), —N($C_1$-$C_6$-alkyl)$_2$, —$SO_2$($C_1$-$C_6$-alkyl), heterocyclyl, heteroaryl, aryl, —O-aryl, —O-heteroaryl, —$CH_2$—NR4R5, —$SO_2$NR4R5, and —C(O)NR4R5,
    where the $C_1$-$C_6$-alkyl substituent may be substituted at least once by $C_1$-$C_6$-alkoxy, fluorine, chlorine, trifluoromethyl, trifluoromethoxy, aryl, heteroaryl, heterocyclyl or OH,
    and the aryl, heteroaryl and heterocyclyl substituents may be substituted at least once by $C_1$-$C_6$-alkyl, $C_1$-$C_6$-alkoxy, fluorine, chlorine, trifluoromethyl, trifluoromethoxy or OH;

aryl 5 to 10-membered aromatic mono- or bicycle;

heteroaryl 5 to 10-membered aromatic mono- or bicyclic heterocycle which comprises one or more heteroatoms selected from N, O and S;

heterocyclyl 5 to 10-membered nonaromatic mono- or bicyclic heterocycle which comprises one or more heteroatoms selected from N, O and S;

R4 and R5 independently of one another selected from the group consisting of:
    hydrogen; unsubstituted or at least monosubstituted $C_1$-$C_{10}$-alkyl, $C_2$-$C_6$-alkenyl, phenyl, indanyl, heterocyclyl and heteroaryl,
    where the substituents are selected from the group consisting of: phenyl, heteroaryl, heterocyclyl, —O-phenyl, fluorine, —CN, —C(O)$NH_2$, —C(O)($C_1$-$C_3$-alkyl), —C(O)-phenyl, —N($C_1$-$C_3$-alkyl)$_2$, —NH($C_1$-$C_3$-alkyl), —$NH_2$, —NH-heteroaryl, —NH—C(O)-heteroaryl, $C_1$-$C_6$-alkyl, $C_1$-$C_3$-alkoxy and hydroxy,
    and the phenyl, heterocyclyl and heteroaryl fragments of these substituents may in turn be at least monosubstituted by fluorine, chlorine, bromine, oxo, —$CF_3$, —$OCF_3$, —$NO_2$, —CN, phenyl, pyridinyl, —NHC(O)($C_1$-$C_3$-alkyl), —COOH, hydroxy, $C_1$-$C_3$-alkyl, $C_1$-$C_3$-alkoxy, —$SO_2NH_2$, —$SO_2$NH($C_1$-$C_3$-alkyl), —$SO_2$N($C_1$-$C_3$-alkyl)$_2$, —C(O)$NH_2$, —C(O)NH($C_1$-$C_3$-alkyl), —C(O)N($C_1$-$C_3$-alkyl)$_2$, —$SO_2$($C_1$-$C_3$-alkyl), —$NH_2$, —NH($C_1$-$C_3$-alkyl) or —N($C_1$-$C_3$-alkyl)$_2$; or R4 and R5 form together with the nitrogen atom to which they are bonded unsubstituted or at least monosubstituted heterocyclyl,
    where the substituents are selected from the group consisting of: phenyl, heteroaryl, heterocyclyl, oxo, fluorine, chlorine, —C(O)($C_1$-$C_3$-alkyl), —C(O)-phenyl and hydroxy,
    and the phenyl, heterocyclyl and heteroaryl fragments of these substituents may in turn be at least monosubstituted by fluorine or $C_1$-$C_3$-alkyl;

or a physiologically tolerated salt thereof;

with the proviso that Ar is not triazinyl or chromanyl, and Ar is not pyridopyrazinyl or naphthyridinyl when X is NH or N($C_1$-$C_3$-alkyl).

DETAILED DESCRIPTION

Where groups, fragments, radicals or substituents such as, for example, aryl, heteroaryl, alkyl, alkoxy etc. are present more than once in the compounds of the formula (I), they all have independently of one another the abovementioned meanings and may thus in each (individual) case have either an identical or a mutually independent meaning. The following statements apply to (for example) aryl and any other radical irrespective of its designation as aryl group, substituent, fragment or radical. A further example is the —N(C$_1$-C$_3$-alkyl)$_2$ group in which the two alkyl substituents may be either identical or different (for example twice ethyl or once propyl and once methyl).

Where a substituent, for example aryl, in the above definitions of compounds of the formula (I) may be unsubstituted or at least monosubstituted by a group of further substituents, for example C$_1$-C$_6$-alkyl, C$_1$-C$_6$-alkoxy, halogen etc., then the selection in those cases where aryl is polysubstituted takes place from the series of further substituents independently of one another. Thus, for example, when aryl is disubstituted, all combinations of the further substituents are included. Aryl may thus be for example disubstituted with ethyl, aryl may in each case be monosubstituted with methyl and ethoxy, aryl may in each case be monosubstituted with ethyl and fluorine, aryl may be disubstituted with methoxy, etc.

Alkyl radicals may be either linear or branched, acyclic or cyclic. This also applies when they are a part of another group such as, for example, alkoxy groups (C$_1$-C$_{10}$-alkyl-O—), alkoxycarbonyl groups or amino groups, or if they are substituted.

Examples of alkyl groups are: methyl, ethyl, propyl, butyl, pentyl, hexyl, heptyl, octyl, nonyl or decyl. Included therein are both the n isomers of these radicals and isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals, such as, for example, aryl, heteroaryl, alkoxy or halogen. It is moreover possible for the additional substituents to occur in any desired position of the alkyl radical. The term alkyl also includes cycloalkyl and cycloalkylalkyl (alkyl which is in turn substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. The ring systems may also, where appropriate, be polycyclic, such as decalinyl, norbornanyl, bornanyl or adamantanyl. The cycloalkyl radicals may be unsubstituted or optionally substituted by one or more further radicals as mentioned above by way of example for the alkyl radicals.

Examples of alkenyl groups are: vinyl, 1-propenyl, 2-propenyl (allyl), 2-butenyl, 2-methyl-2-propenyl, 3-methyl-2-butenyl. The term alkenyl here expressly also includes cycloalkenyl radicals and cycloalkenylalkyl radicals (alkyl which is substituted by cycloalkenyl) which comprise at least three carbon atoms. Examples of cycloalkenyl are: cyclopentenyl, cyclohexenyl, cycloheptenyl and cyclooctenyl.

The alkenyl radicals may have one to three conjugated or non-conjugated double bonds (that is to say also alk-dienyl and alk-trienyl radicals), preferably one double bond in a linear or branched chain. The alkenyl radicals may be unsubstituted or optionally substituted by one or more further radicals as mentioned above by way of example for the alkyl radicals.

Unless stated otherwise, the aforementioned aryl, heteroaryl and heterocyclyl radicals may either unsubstituted or have one or more, for example 1, 2, 3 or 4 further, of the aforementioned substituents in any desired position. For example, the substituent in monosubstituted phenyl radicals may be in position 2, 3 or 4, the substituents in disubstituted phenyl radicals may be in the 2,3 position, 2,4 position, 2,5 position, 2,6 position, 3,4 position or 3,5 position. The substituents in trisubstituted phenyl radicals may be in the 2,3,4 position, 2,3,5 position, 2,3,6 position, 2,4,5 position, 2,4,6 position or the 3,4,5 position. The substituents in tetrasubstituted phenyl radicals may be in the 2,3,4,5 position, the 2,3, 4,6 position or in the 2,3,5,6 position.

The aforementioned and the following definitions relating to monovalent radicals apply in exactly the same way to divalent radicals such as phenylene, naphthylene or heteroarylene. These divalent radicals (fragments) may be linked to the adjacent groups for any desired ring carbon atom. In the case of phenylene radicals, this may be in the 1,2 position (ortho-phenylene), 1,3 position (meta-phenylene) or 1,4 position (para-phenylene). In the case of a 5-membered aromatic system comprising a heteroatom, such as, for example, thiophene or furan, the two free bonds may be in the 2,3 position, 2,4 position, 2,5 position or 3,4 position. A divalent radical derived from a 6-membered aromatic system having a heteroatom, such as, for example, pyridine, may be a 2,3-, 2,4-, 2,5-, 2,6-, 3,4- or 3,5-pyridinediyl radical. In the case of nonsymmetrical divalent radicals, the present invention also includes all positional isomers, i.e. in the case of, for example, a 2,3-pyridinediyl radical the compound in which one adjacent group is located in position 2 and the other adjacent group is located in position 3 is included just as much as the compound in which one adjacent group is located in position 3 and the other adjacent group is located in position 2.

Unless stated otherwise, heteroaryl radicals heteroarylene radicals, heterocyclyl radicals and heterocyclylene radicals, and rings which are formed by two groups bonded to nitrogen, are preferably derived from completely saturated, partly or wholly unsaturated heterocycles (i.e. heterocycloalkanes, heterocycloalkenes, heteroaromatics) which comprise 1, 2, 3 or 4 heteroatoms which may be either different or identical. They are preferably derived from heterocycles which comprise 1, 2 or 3, particularly preferably 1 or 2, heteroatoms which may be identical or different. Unless stated otherwise, the heterocycles are mono- or polycyclic, for example monocyclic, bicyclic or tricyclic. They are preferably monocyclic or bicyclic. 5-Membered, 6-membered or 7-membered rings are preferred, and 5-membered or 6-membered rings are particularly preferred. In the case of polycyclic heterocycles having 2 and more heteroatoms, these may occur all in the same ring or be distributed over a plurality of rings.

Radicals referred to as heteroaryl in the present invention are derived from monocyclic or bicyclic aromatic heterocycles. Examples of heteroaryl are: pyrrolyl, furanyl (=furyl), thiophenyl (=thienyl), imidazolyl, pyrazolyl, 1,2,3-triazolyl, 1,2,4-triazolyl, 1,3-oxazolyl (=oxazolyl), 1,2-oxazolyl (=isoxazolyl), oxadiazolyl, 1,3-thiazolyl (=thiazolyl), 1,2-thiazolyl (=isothiazolyl), tetrazolyl, pyridinyl (=pyridyl), pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, quinolinyl, isoquinolinyl, quinazolinyl, quinoxalinyl, phthalazinyl, thienothiophenyl, 1,8-naphthyridinyl, other naphthyridinyls, pteridinyl or thiazolo[3,2-b][1,2,4]-triazolyl. Where the systems are non-monocyclic, also included for the second ring for each of the abovementioned heteroaryls is the saturated form (perhydro form) or the partly unsaturated form (for example the dihydro form or tetrahydro form) or the maximally unsaturated (nonaromatic) form, as long as the respective forms are known and stable. The term heteroaryl thus includes in the present invention for example also bicyclic radicals in which either both rings are aromatic or bicyclic radicals in which only one ring is aromatic. Such examples of heteroaryl are: 3H-indolinyl, 2(1H)-quinolinonyl, 4-oxo-1,4-dihydroquinolinyl, 2H-1-oxoisoquinolyl, 1,2-dihydroquinolinyl, 3,4-dihydroquinolinyl, 1,2-dihydroisoquinolinyl, 3,4-dihydroisoquinolinyl, chromonyl, chromanyl, 1,3-benzodioxolyl, oxindolyl, 1,2,3,4-tetrahydroisoquinolinyl, 1,2,3,4-tetrahydroquinolinyl, 5,6-dihydroquinolinyl, 5,6-dihydroisoquinolyl, 5,6,7,8-tetrahydroquinolinyl or 5,6,7,8-tetrahydroisoquinolyl.

Radicals referred to as heterocyclyl in the present invention are derived from monocyclic or bicyclic nonaromatic heterocycles. Nonaromatic heterocycles mean hereinafter in particular heterocycloalkanes (completely saturated heterocycles) and heterocycloalkenes (partly unsaturated heterocycles). In the case of the heterocycloalkenes, also included are compounds having two or more double bonds, which may optionally also be conjugated together. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl, 1,3-dioxolanyl, 1,4-dioxinyl, pyranyl, thiopyranyl, tetrahydro-1,2-oxazinyl, tetrahydro-1,3-oxazinyl, morpholinyl, thiomorpholinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, azepanyl, 2-oxoazepanyl, 1,2,3,4-tetrahydropyridinyl, 1,2-dihydropyridinyl, 1,4-dihydropyridinyl, 1,2,3,6-tetrahydropyridinyl, 4(3H)-pyrimidonyl, 1,4,5,6-tetrahydropyrimidinyl, 2-pyrrolinyl, 3-pyrrolinyl, 2-imidazolinyl, 2-pyrazolinyl, 3,4-dihydro-2H-pyranyl, dihydrofuranyl, 7-oxabicyclo[2.2.1]heptenyl, dihydro-thiophenyl and dihydrothiopyranyl. The degree of saturation of heterocyclic groups is indicated in the respective definition.

Substituents derived from these heterocycles may be linked via any suitable carbon atom, and be provided with further substituents. Radicals derived from nitrogen-containing heterocycles may have a hydrogen atom or another substituent on the corresponding nitrogen atom. Examples include pyrrole, imidazole, pyrrolidine, morpholine, piperazine radicals etc. These nitrogen-containing heterocyclic radicals may also be linked via the ring nitrogen atom, especially if the corresponding heterocyclic radical is linked to a carbon atom. For example, a thienyl radical may be in the form of 2-thienyl or 3-thienyl, a piperidinyl radical in the form of 1-piperidinyl (piperidino), 2-piperidinyl, 3-piperidinyl or 4-piperidinyl. Suitable nitrogen-containing heterocycles may also be in the form of N-oxides or of quaternary salts which have a counter ion which is derived from a physiologically acceptable acid. For example, pyridyl radicals may be in the form of pyridine N-oxides. Suitable sulfur-containing heterocycles may also be in the form of S-oxide or S—S-dioxide.

Radicals referred to as aryl in the present invention are derived from monocyclic or bicyclic aromatic systems which comprise no ring heteroatoms. Where the systems are non-monocyclic, also for the second ring in the term aryl is the saturated form (perhydro form) or the partly unsaturated form (for example the dihydro form or tetrahydro form), as long as the respective forms are known and stable. The term aryl also includes in the present invention for example bicyclic radicals in which either both rings are aromatic or bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl.

Arylalkyl (such as aryl-($C_1$-$C_6$-alkyl)-) means that an alkyl radical (such as $C_1$-$C_6$-alkyl) is in turn substituted by an aryl radical. Heteroarylalkyl (such as heteroaryl-($C_1$-$C_6$-alkyl)-) means that an alkyl radical (such as $C_1$-$C_6$-alkyl) is in turn substituted by a heteroaryl radical. Heterocyclylalkyl (such as heterocyclyl-($C_1$-$C_6$-alkyl)-) means that an alkyl radical (such as $C_1$-$C_6$-alkyl) is in turn substituted by a heterocyclyl radical. Reference is made to the foregoing definitions for the definitions and possible substitutions of alkyl, heteroaryl, heterocyclyl and aryl.

Halogen is fluorine, chlorine, bromine or iodine, is preferably fluorine, chlorine or bromine, and is particularly preferably fluorine or chlorine.

The present invention includes all stereoisomeric forms of compounds of the formula (I). Asymmetric carbon atoms in compounds of the formula (I) may have independently of one another S configurations or R configurations. The invention includes all possible enantiomers and diastereomers and mixtures of two or more stereoisomers, for example mixtures of enantiomers and/or diastereomers, in all amounts and ratios. It is thus possible for compounds of the present invention which exist as enantiomers to be in enantiopure form, both as dextrorotatory and levorotatory antipodes, in the form of racemates and in the form of mixtures of the two enantiomers in all ratios. In the case of cis/trans isomers, the invention includes both the cis form and the trans form, and mixtures of these forms in all ratios. The present invention relates to all these forms. Preparation of the individual stereoisomers is possible if desired by separating a mixture by conventional methods, for example by chromatography or crystallization, through the use of stereochemically pure starting materials for the synthesis or by stereoselective synthesis. It is also possible alternatively to carry out a derivatization before separating the stereoisomers. Separation of a mixture of stereoisomers can be carried out with the compounds of the formula (I) or with the appropriate intermediates during the synthesis. The present invention further includes also all tautomeric forms of compounds according to formula (I), in particular keto/enol tautomerism, i.e. the corresponding compounds may be either in their keto form or in their enol form or in mixtures thereof in all the ratios.

Where the compounds of formula (I) comprise one or more acidic or basic groups, the present invention also includes the correspondingly physiologically or toxicologically acceptable salts.

Physiologically acceptable salts are, because their solubility in water is greater than that of the starting or basic compounds, particularly suitable for medical applications. These salts must have a physiologically acceptable anion or cation. Suitable physiologically acceptable acid addition salts of the compounds of the invention are salts of inorganic acids such as hydrochloric acid, hydrobromic, phosphoric, metaphosphoric, nitric, sulfonic and sulfuric acids, and organic acids such as, for example, acetic acid, theophyllineacetic acid, methylenebis-b-oxynaphthonic, benzenesulfonic, benzoic, citric, ethanesulfonic, salicylic, fumaric, gluconic, glycolic, isethionic, lactic, lactobionic, maleic, malic, methanesulfonic, succinic, p-toluenesulfonic, tartaric and trifluoroacetic acids. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the framework of the invention as useful intermediates for preparing or purifying pharmaceutically acceptable salts and/or for use in non-therapeutic, for example in vitro, applications.

Where compounds of the formula (I) comprise both acidic and basic groups in the same molecule, the present invention includes—in addition to the salt forms detailed previously—also inner salts or betaines (zwitterions).

The corresponding salts of the compounds according to formula (I) can be obtained by conventional methods which are known to the skilled worker, for example by reacting with an organic or inorganic acid or base in a solvent or dispersant, or by anion or cation exchange with other salts.

The present invention additionally includes all solvates of compounds of the formula (I), for example hydrates or adducts with alcohol, active metabolites of compounds of the formula (I), and derivatives which comprise a physiologically acceptable group which can be eliminated, for example esters or amides.

The term "physiologically functional derivative" used herein refers to any physiologically acceptable derivative of a compound of the invention of the formula I, e.g. an ester which, on administration to a mammal such as, for example, a human, is able (directly or indirectly) to form a compound of the formula I or an active metabolite thereof.

Physiologically functional derivatives also include prodrugs of the compounds of the invention. Such prodrugs may be metabolized in vivo to a compound of the invention. These prodrugs may themselves be active or not and the present invention likewise relates to them.

The compounds of the invention may also exist in various polymorphous forms, e.g. as amorphous and crystalline polymorphous forms. All polymorphous forms of the compounds of the invention belong within the framework of the invention and are a further aspect of the invention.

Preferred compounds of the general formula (I) are those compounds in which one, more than one or all of the aforementioned substituents R1 to R5, X, Ar, heteroaryl, heterocyclyl and aryl have independently of one another the meanings (definitions) detailed below, and the present invention relates to all possible combinations of preferred, more preferred, and particularly preferred meanings (definitions), likewise in combination with the substituents in their above-mentioned meaning.

X is preferably O, NH or $N(C_1-C_3$-alkyl);
X is more preferably NH or $N(C_1-C_3$-alkyl) and particularly preferably NH or N-methyl;
R1 is preferably fluorine, —$OCF_3$ or $C_1-C_4$-alkyl;
R1 is more preferably $C_1-C_3$-alkyl and particularly preferably ethyl;
R2 is preferably hydrogen, fluorine, —$OCF_3$ or $C_1-C_4$-alkyl;
R2 is more preferably hydrogen;
R3 is preferably fluorine, —$OCF_3$ or $C_1-C_4$-alkyl;
R3 is more preferably $C_1-C_3$-alkyl and particularly preferably methyl;
Ar is preferably unsubstituted or monosubstituted phenyl or heteroaryl, where the substituents are selected from the group consisting of:
fluorine, chlorine, —$CF_3$, —$OCF_3$, —CN, —$C(O)(C_1-C_3$-alkyl), $NH_2$, —$NHC(O)(C_1-C_3$-alkyl), hydroxy, oxo, $C_1-C_3$-alkyl, $C_1-C_3$-alkoxy, —$NH(C_1-C_3$-alkyl), —$N(C_1-C_3$-alkyl)$_2$, —$SO_2(C_1-C_3$-alkyl), heterocyclyl, heteroaryl, aryl, —O-aryl, —O-heteroaryl, —$CH_2NR4R5$ and —$C(O)NR4R5$, where the $C_1-C_3$-alkyl substituent may be at least monosubstituted by $C_1-C_3$-alkoxy, fluorine, chlorine, trifluoromethyl, trifluoromethoxy, aryl, heteroaryl, heterocyclyl or OH,
and the aryl, heteroaryl and heterocyclyl substituents may be at least monosubstituted by $C_1-C_3$-alkyl, $C_1-C_3$-alkoxy, fluorine, chlorine, trifluoromethyl, trifluoromethoxy or OH;
Ar is more preferably unsubstituted or at least monosubstituted phenyl, indanyl, naphthyl, indolyl, benzofuranyl, benzimidazolyl, furanyl, thienyl, imidazolyl, pyrimidinyl, pyrazolyl, naphthyl, isoquinolinyl, pyridinyl, quinolinyl, 2,3-dihydroindolyl, 5,6,7,8-tetrahydronaphthyl where the substituents are selected from the group consisting of:
fluorine, chlorine, —$CF_3$, —$OCF_3$, —CN, —$C(O)(C_1-C_3$-alkyl), $NH_2$, —$NHC(O)(C_1-C_3$-alkyl), hydroxy, oxo, $C_1-C_3$-alkyl, $C_1-C_3$-alkoxy, —$NH(C_1-C_3$-alkyl), —$N(C_1-C_3$-alkyl)$_2$, —$SO_2(C_1-C_3$-alkyl), heteroaryl, phenyl, —O-phenyl, —O-heteroaryl, —$CH_2NR4R5$, —$SO_2NR4R5$ and —$C(O)NR4R5$,
where the $C_1-C_3$-alkyl substituent may be at least monosubstituted by $C_1-C_3$-alkoxy, fluorine, chlorine, trifluoromethyl, trifluoromethoxy, phenyl, heteroaryl or OH,
and the phenyl and heteroaryl substituents may be at least monosubstituted by $C_1-C_3$-alkyl, $C_1-C_3$-alkoxy, fluorine, chlorine, trifluoromethyl, trifluoromethoxy or OH;
Ar is particularly preferably unsubstituted or monosubstituted phenyl, pyridyl, quinolinyl, indanyl, 2,3-dihydroindolyl, 5,6,7,8-tetrahydronaphthyl, where the substituents are selected from the group consisting of:
—CN, —$C(O)(C_1-C_3$-alkyl), —$NHC(O)(C_1-C_3$-alkyl), oxo, $C_1-C_3$-alkyl, $C_1-C_3$-alkoxy, —$SO_2(C_1-C_3$-alkyl), heteroaryl, —O-heteroaryl, —$CH_2$—$NR4R5$, —$SO_2$—$NR4R5$, and —$C(O)NR4R5$,
where the $C_1-C_3$-alkyl substituent may be monosubstituted by heteroaryl or OH, and the heteroaryl substituent may be monosubstituted by $C_1-C_3$-alkyl;
R4 is preferably hydrogen or $C_1-C_3$-alkyl;
R4 is more preferably hydrogen,
R5 is preferably selected from the group consisting of: hydrogen; unsubstituted or at least monosubstituted $C_1-C_6$-alkyl, cyclohexenyl, indanyl, phenyl, pyrrolidinyl, pyrrolyl, pyrazolyl, furanyl and piperidinyl, where the substituents are selected from the group consisting of: fluorine, —CN, —$C(O)NH_2$, —O-phenyl, —C(O)-phenyl, —$N(CH_3)_2$, $C_1-C_3$-alkyl, $C_1-C_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, whose substituents are in turn selected from the group consisting of: fluorine, chlorine, oxo, $CF_3$, —$OCF_3$, —$NO_2$, phenyl, pyridinyl, —$NHC(O)CH_3$, —COOH, hydroxy, $C_1-C_3$-alkyl, $C_1-C_3$-alkoxy, —$SO_2NH_2$, —$C(O)NH_2$ and —$N(CH_3)_2$;
R5 is more preferably selected from the group consisting of: hydrogen; unsubstituted or monosubstituted $C_1-C_6$-alkyl, cyclohexenyl, indanyl, phenyl, pyrrolidinyl, pyrrolyl, pyrazolyl, furanyl and piperidinyl,
where the substituents are selected from the group consisting of: fluorine, —CN, —$C(O)NH_2$, —O-phenyl, —C(O)-phenyl, —$N(CH_3)_2$, $C_1-C_3$-alkyl, $C_1-C_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, whose substituents are in turn selected from the group consisting of: fluorine, chlorine, oxo, $CF_3$, —$OCF_3$, —$NO_2$, phenyl, pyridinyl, —$NHC(O)CH_3$, —COOH, hydroxy, $C_1-C_3$-alkyl, $C_1-C_3$-alkoxy, —$SO_2NH_2$, —$C(O)NH_2$ and —$N(CH_3)_2$;
R5 is particularly preferably hydrogen, $C_1-C_3$ alkyl or pyridinyl
R4 and R5 form preferably together with the nitrogen atom to which they are bonded a radical selected from the group consisting of: unsubstituted or at least monosubstituted piperidinyl, pyrrolidinyl, morpholinyl and piperazinyl, where the substituents are selected from the group consisting of: fluorine, —C(O)—($C_1$-$C_3$-alkyl), oxo, $C_1$-$C_3$-alkyl, hydroxy, unsubstituted or at least monosubstituted phenyl, imidazolyl, pyridinyl, pyrimidinyl, piperidinyl and pyrrolidinyl, whose substituents are turn fluorine or $C_1$-$C_3$-alkyl;

R4 and R5 form more preferably together with the nitrogen atom to which they are bonded a pyrrolidinyl radical;

aryl is preferably phenyl, indanyl or naphthyl;

aryl is more preferably phenyl or indanyl;

aryl is particularly preferably phenyl;

heteroaryl is preferably pyridinyl, thienyl, pyrimidinyl, imidazolyl, furanyl, indolyl, benzimidazolyl, pyrazolyl, 1,3-benzodioxolyl, triazolyl, thiazolyl, isoxazolyl, pyrrolyl, pyrazinyl, oxazolyl, pyridazinyl, quinolinyl, isoquinolinyl, benzofuranyl, 3-oxo-1,3-dihydroisobenzofuranyl, 2,3-dihydroindolyl or 4,5,6,7-tetrahydrobenzothiazolyl;

heteroaryl is more preferably pyridinyl, quinolinyl, indolyl, benzofuranyl, thienyl, pyrimidinyl, imidazolyl, furanyl, benzimidazolyl, pyrazolyl, thiazolyl, isoquinolinyl, pyrrolyl or 2,3-dihydroindolyl;

heteroaryl is particularly preferably pyridinyl, imidazolyl; or pyrimidinyl;

heterocyclyl is preferably morpholinyl, pyrrolidinyl, piperidinyl, tetrahydropyranyl, thiazolidinyl, dihydroisoxazolyl, piperazinyl or tetrahydrofuranyl;

heterocyclyl is more preferably morpholinyl, pyrrolidinyl, piperidinyl or piperazinyl;

heterocyclyl is particularly preferably pyrrolidinyl.

The invention also relates to compounds of the formula I in which the meanings are:

X O, NH or N($C_1$-$C_3$-alkyl);

R1 fluorine, —$OCF_3$ or $C_1$-$C_4$-alkyl;

R2 hydrogen, fluorine, —$OCF_3$ or $C_1$-$C_4$-alkyl;

R3 fluorine, —$OCF_3$ or $C_1$-$C_4$-alkyl;

Ar unsubstituted or monosubstituted phenyl or heteroaryl,
where the substituents are selected from the group consisting of:
fluorine, chlorine, —$CF_3$, —$OCF_3$, —CN, —C(O)($C_1$-$C_3$-alkyl), $NH_2$, —NHC(O)($C_1$-$C_3$-alkyl), hydroxy, oxo, $C_1$-$C_3$-alkyl, $C_1$-$C_3$-alkoxy, —NH($C_1$-$C_3$-alkyl), —N($C_1$-$C_3$-alkyl)$_2$, —$SO_2$($C_1$-$C_3$-alkyl), heterocyclyl, heteroaryl, aryl, —O-aryl, —O-heteroaryl, —$CH_2$—NR4R5, —$SO_2$—NR4R5, and —C(O)NR4R5,
where the $C_1$-$C_3$-alkyl substituent may be at least monosubstituted by $C_1$-$C_3$-alkoxy, fluorine, chlorine, trifluoromethyl, trifluoromethoxy, aryl, heteroaryl, heterocyclyl or OH,
and the aryl, heteroaryl and heterocyclyl substituents may be at least monosubstituted by $C_1$-$C_3$-alkyl, $C_1$-$C_3$-alkoxy, fluorine, chlorine, trifluoromethyl, trifluoromethoxy or OH;

R4 hydrogen or $C_1$-$C_3$-alkyl;

R5 is selected from the group consisting of; hydrogen; unsubstituted or at least monosubstituted $C_1$-$C_6$-alkyl, cyclohexenyl, indanyl, phenyl, pyrrolidinyl, pyrrolyl, pyrazolyl, furanyl and piperidinyl,
where the substituents are selected from the group consisting of: fluorine, —CN, —C(O)$NH_2$, —O-phenyl, —C(O)-phenyl, —N($CH_3$)$_2$, $C_1$-$C_3$-alkyl, $C_1$-$C_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, whose substituents are in turn selected from the group consisting of:
fluorine, chlorine, oxo, $CF_3$, —$OCF_3$, —$NO_2$, phenyl, pyridinyl, —NHC(O)$CH_3$, —COOH, hydroxy, $C_1$-$C_3$-alkyl, $C_1$-$C_3$-alkoxy, —$SO_2NH_2$, —C(O)$NH_2$ and —N($CH_3$)$_2$; or R4 and R5 form together with the nitrogen atom to which they are bonded a radical selected from the group consisting of: unsubstituted or at least monosubstituted piperidinyl, pyrrolidinyl, morpholinyl and piperazinyl, where the substituents are selected from the group consisting of: fluorine, —C(O)($C_1$-$C_3$-alkyl), oxo, $C_1$-$C_3$-alkyl, hydroxy, unsubstituted or at least monosubstituted phenyl, imidazolyl, pyridinyl, pyrimidinyl, piperidinyl and pyrrolidinyl, whose substituents are in turn fluorine or $C_1$-$C_3$-alkyl;

aryl phenyl, indanyl or naphthyl;

heteroaryl pyridinyl, thienyl, pyrimidinyl, imidazolyl, furanyl, indolyl, benzimidazolyl, pyrazolyl, 1,3-benzodioxolyl, triazolyl, thiazolyl, isoxazolyl, pyrrolyl, pyrazinyl, oxazolyl, pyridazinyl, quinolinyl, isoquinolinyl, benzofuranyl, 3-oxo-1,3-dihydroisobenzofuranyl, 2,3-dihydroindolyl or 4,5,6,7-tetrahydrobenzothiazolyl;

heterocyclyl morpholinyl, pyrrolidinyl, piperidinyl, tetrahydropyranyl, thiazolidinyl, dihydroisoxazolyl, piperazinyl or tetrahydrofuranyl;

and the physiologically tolerated salts thereof.

The invention further relates to compounds of the formula I in which the meanings are:

X NH or N($C_1$-$C_3$-alkyl);

R1 $C_1$-$C_3$-alkyl;

R2 hydrogen;

R3 $C_1$-$C_3$-alkyl;

Ar unsubstituted or monosubstituted phenyl, indolyl, benzofuranyl, benzimidazolyl, furanyl, thienyl, imidazolyl, pyrimidinyl, pyrazolyl, isoquinolinyl, pyridinyl, quinolinyl, or 2,3-dihydroindolyl,
where the substituents are selected from the group consisting of: fluorine, chlorine, —$CF_3$, —$OCF_3$, —CN, —C(O)($C_1$-$C_3$-alkyl), $NH_2$, —NHC(O)($C_1$-$C_3$-alkyl), hydroxy, oxo, $C_1$-$C_3$-alkyl, $C_1$-$C_3$-alkoxy, —NH($C_1$-$C_3$-alkyl), —N($C_1$-$C_3$-alkyl)$_2$, —$SO_2$($C_1$-$C_3$-alkyl), heteroaryl, phenyl, —O-phenyl, —O-heteroaryl, —$CH_2$—NR4R5, —$SO_2$—NR4R5, and —C(O)NR4R5,
where the $C_1$-$C_3$-alkyl substituent may be at least monosubstituted by $C_1$-$C_3$-alkoxy, fluorine, chlorine, trifluoromethyl, trifluoromethoxy, phenyl, heteroaryl or OH,
and the phenyl and heteroaryl substituents may be at least monosubstituted by $C_1$-$C_3$-alkyl, $C_1$-$C_3$-alkoxy, fluorine, chlorine, trifluoromethyl, trifluoromethoxy or OH;

R4 hydrogen

R5 is selected from the group consisting of;
hydrogen; unsubstituted or monosubstituted $C_1$-$C_6$-alkyl, cyclohexenyl, indanyl, phenyl, pyrrolidinyl, pyrrolyl, pyrazolyl, furanyl and piperidinyl, where the substituents are selected from the group consisting of: fluorine, —CN, —C(O)$NH_2$, -O-phenyl, —C(O)-phenyl, —N($CH_3$)$_2$, $C_1$-$C_3$-alkyl, $C_1$-$C_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, whose substituents are in turn selected from the group consisting of: fluorine, chlorine, oxo, $CF_3$, —$OCF_3$, —$NO_2$, phenyl, pyridinyl, —NHC(O)$CH_3$, —COOH, hydroxy, $C_1$-$C_3$-alkyl, $C_1$-$C_3$-alkoxy, —$SO_2NH_2$, —C(O)$NH_2$ and —N($CH_3$)$_2$; or R4 and R5 form together with the nitrogen atom to which they are bonded an unsubstituted or at least monosubstituted pyrrolidinyl radical, where the substituents are selected from the group consisting of: $C_1$-$C_3$-alkyl and hydroxy;
aryl phenyl or indanyl;
heteroaryl pyridinyl, quinolinyl, indolyl, benzofuranyl, thienyl, pyrimidinyl, imidazolyl, furanyl, benzimidazolyl, pyrazolyl, thiazolyl, isoquinolinyl, pyrrolyl or 2,3-dihydroindolyl;
and the physiologically tolerated salts thereof.

The invention also relates to compounds of the formula I in which the meanings are:
X NH or N-methyl;
R1 ethyl;
R2 hydrogen;
R3 methyl;
Ar unsubstituted or monosubstituted phenyl, indanyl, 5,6,7, 8-tetra-hydronaphthyl, pyridinyl, quinolinyl, or 2,3-dihydroindolyl,
  where the substituents are selected from the group consisting of: —CN, —C(O)($C_1$-$C_3$-alkyl), —NHC(O)($C_1$-$C_3$-alkyl), oxo, $C_1$-$C_3$-alkyl, $C_1$-$C_3$-alkoxy, —$SO_2$($C_1$-$C_3$-alkyl), heteroaryl, —O-heteroaryl, —$CH_2$—NR4R5, —$SO_2$—NR4R5, and —C(O)NR4R5,
  where the $C_1$-$C_3$-alkyl substituent may be monosubstituted by heteroaryl or OH,
  and the heteroaryl substituent may be monosubstituted by $C_1$-$C_3$-alkyl;
R4 hydrogen
R5 hydrogen, $C_1$-$C_3$-alkyl) or pyridinyl;
R4 and R5 form together with the nitrogen atom to which they are bonded a pyrrolidinyl radical;
heteroaryl pyridinyl, imidazolyl, or pyrimidinyl;
and the physiologically tolerated salts thereof.

The invention also relates to compounds of the general formula I selected from the group consisting of:
3-(5-ethyl-2-methyl-6-oxo-1,6-dihydropyridin-3-ylamino) benzonitrile;
3-(5-ethyl-2-methyl-6-oxo-1,6-dihydropyridin-3-ylamino) benzamide;
5-(3-acetylphenylamino)-3-ethyl-6-methyl-1H-pyridin-2-one;
N-[3-(5-ethyl-2-methyl-6-oxo-1,6-dihydropyridin-3-ylamino)phenyl]acetamide;
3-ethyl-6-methyl-5-(quinolin-3-ylamino)-1H-pyridin-2-one;
4-(5-ethyl-2-methyl-6-oxo-1,6-dihydropyridin-3-ylamino) benzenesulfonamide;
3-ethyl-6-methyl-5-[4-(pyridin-3-yloxy)phenylamino]-1H-pyridin-2-one;
3-ethyl-5-(4-imidazol-1-ylphenylamino)-6-methyl-1H-pyridin-2-one;
5-(1-acetyl-2,3-dihydro-1H-indol-6-ylamino)-3-ethyl-6-methyl-1H-pyridin-2-one;
4-(5-ethyl-2-methyl-6-oxo-1,6-dihydropyridin-3-ylamino)-N-pyridin-2-yl-benzenesulfonamide;
3-ethyl-6-methyl-5-(5-oxo-5,6,7,8-tetrahydronaphthalen-2-ylamino)-1H-pyridin-2-one;
N-[6-(5-ethyl-2-methyl-6-oxo-1,6-dihydropyridin-3-ylamino)pyridin-3-yl]-acetamide;
6-(5-ethyl-2-methyl-6-oxo-1,6-dihydropyridin-3-ylamino) nicotinonitrile;
3-ethyl-6-methyl-5-(1-oxoindan-5-ylamino)-1H-pyridin-2-one;
3-ethyl-6-methyl-5-(pyridin-4-ylamino)-1H-pyridin-2-one;
3-ethyl-6-methyl-5-(pyridin-2-ylamino)-1H-pyridin-2-one;
5-(2-acetylphenylamino)-3-ethyl-6-methyl-1H-pyridin-2-one;
5-(4-acetylphenylamino)-3-ethyl-6-methyl-1H-pyridin-2-one;
3-ethyl-6-methyl-5-(pyridin-3-ylamino)-1H-pyridin-2-one;
3-ethyl-5-(3-methoxyphenoxy)-6-methyl-1H-pyridin-2-one;
3-(5-ethyl-2-methyl-6-oxo-1,6-dihydropyridin-3-yloxy) benzonitrile;
3-ethyl-6-methyl-5-(3-methylaminomethylphenylamino)-1H-pyridin-2-one;
3-ethyl-5-(3-hydroxymethylphenylamino)-6-methyl-1H-pyridin-2-one;
3-ethyl-5-(3-methanesulfonylphenylamino)-6-methyl-1H-pyridin-2-one;
3-ethyl-6-methyl-5-[3-(2-methylpyrimidin-4-yl)phenylamino]-1H-pyridin-2-one;
3-ethyl-6-methyl-5-(3-pyrrolidin-1-ylmethylphenylamino)-1H-pyridin-2-one;
3-ethyl-5-[3-(1-hydroxyethyl)phenylamino]-6-methyl-1H-pyridin-2-one;
3-ethyl-6-methyl-5-(methylphenylamino)-1H-pyridin-2-one;
and the physiologically tolerated salts thereof.

If the compounds of the formula I comprise one or more acidic or basic groups or one or more basic heterocycles, the corresponding physiologically or toxicologically acceptable salts also belong to the invention, especially the pharmaceutically usable salts. Thus, the compounds of the formula I having acidic groups, e.g. one or more COOH groups, can be used for example as alkali metal salts, preferably sodium or potassium salts, or as alkaline earth metal salts, e.g. calcium or magnesium salts, or as ammonium salts, e.g. as salts with ammonia or organic amines or amino acids. Compounds of the formula I having one or more basic, i.e. protonatable, groups or comprising one or more basic heterocyclic rings can also be used in the form of their physiologically tolerated acid addition salts with inorganic or organic acids, for example as hydrochlorides, phosphates, sulfates, methanesulfonates, acetates, lactates, maleates, fumarates, malates, gluconates etc. If the compounds of the formula I comprise both acidic and basic groups in the molecule, then, besides the salt forms described, also inner salts, called betaines, belong to the invention. Salts can be obtained from the compounds of the formula I by customary methods, for example by combining with an acid or base in a solvent or dispersant or else by anion exchange from other salts.

The compounds of the formula I may, if substituted appropriately, exist in stereoisomeric forms. If the compounds of the formula I contain one or more centers of asymmetry, these may have independently of one another the S configuration or the R configuration. The invention includes all possible stereoisomers, e.g. enantiomers or diastereomers, and mixtures of two or more stereoisomeric forms, e.g. enantiomers and/or diastereomers, in any ratios. Enantiomers for example thus belong in enantiopure form, both as levorotatory and as dextrorotatory antipodes, and in the form of mixtures of the two enantiomers in different ratios or in the form of racemates to the invention. Individual stereoisomers can be prepared if desired by fractionating a mixture by customary methods or, for example, by stereoselective synthesis. If mobile hydrogen atoms are present, the present invention also includes tautomeric forms of the compounds of the formula I.

The compounds of the formula I can be prepared by various chemical methods which likewise belong to the present invention. Some typical routes are outlined in the reaction sequences referred to below as schemes 1 to 3. Substituents R are in each case defined as indicated above unless indicated otherwise hereinafter. The starting compounds and the intermediates are either commercially available or can be prepared by methods known to the skilled worker.

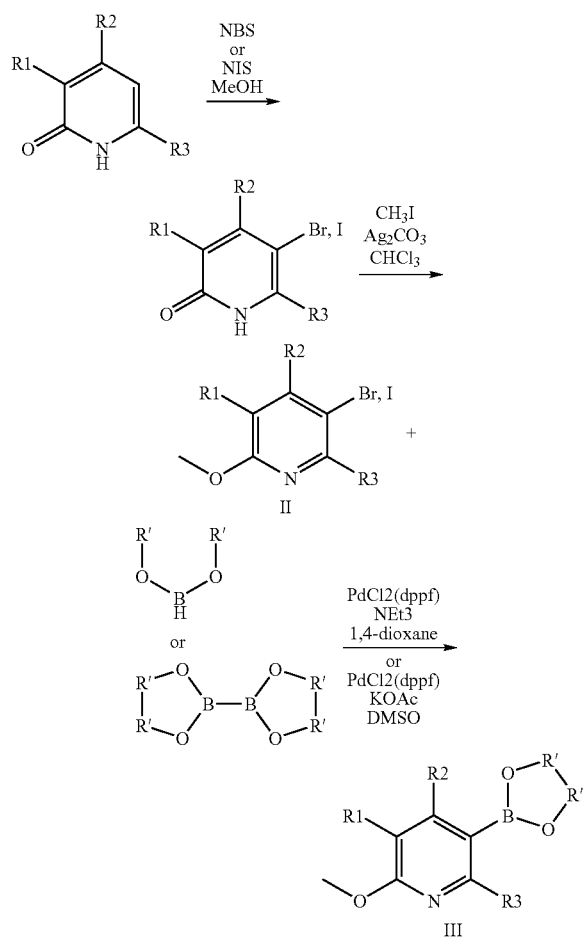

R' = alkyl radical, R', R' may also together form a ring

Thus, for example, a compound of the formula I is obtained from intermediates II or III (possible preparations are described in scheme 1) as shown in schemes 2 and 3.

Intermediate II can be prepared from an appropriately R1-, R2- and R3-substituted 2(1H)-pyridone by bromination or iodination (which can be carried out for example with N-bromosuccinimide or N-iodosuccinimide in methanol as solvent) and subsequent O-alkylation (for example by methyl iodide in dichloromethane with the addition of silver carbonate). For example, 3-ethyl-6-methyl-2(1H)-pyridone is chosen as starting material to prepare compounds with R1 equal to ethyl, R2 equal to hydrogen and R3 equal to methyl. According to the desired radicals for R1-R3 it is possible to employ other appropriately substituted 2(1H)-pyridones as starting materials.

Intermediate III can be prepared from intermediate II by palladium-catalyzed borylation (for example by reaction with bis(pinacolato)diboron or 4,4,5,5-tetramethyl-1,3,2-dioxaborolane with palladium dichloride 1,1'-bis(diphenylphosphino)ferrocene as catalyst and potassium acetate or triethylamine as base in dimethyl sulfoxide or 1,4-dioxane as solvent).

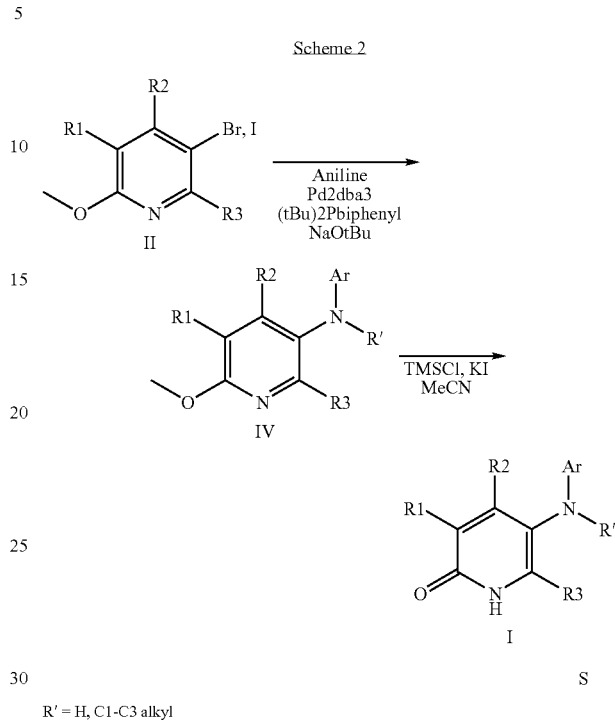

R' = H, C1-C3 alkyl

Compounds of the formula IV can be prepared by palladium-catalyzed Buchwald-Hartwig amination with an aniline (scheme 2). Elimination of the methyl group from the compounds of the formula IV (for example by trimethylchlorosilane and potassium iodide in acetonitrile) affords the pyridones of the formula I.

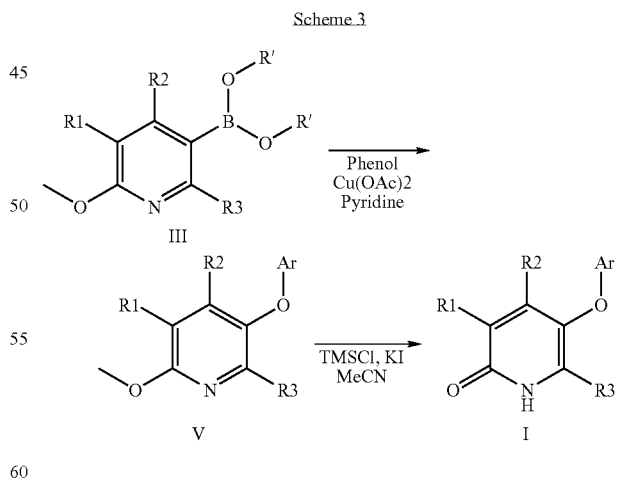

Preparation of compounds of the formula V can start from intermediate III which is reacted by copper-catalyzed coupling with phenols (e.g. in pyridine) (scheme 3). Elimination of the methyl group from the compounds of the formula V (for example by trimethylchlorosilane and potassium iodide in acetonitrile) affords the pyridones of the formula I.

The anilines and phenols employed in scheme II and III can be purchased or synthesized by acids known from the literature.

In may be appropriate in all procedures for functional groups in the molecule to be protected temporarily in certain reaction methods. Such protective groups are familiar to the skilled worker. The selection of a protective group for groups which come into consideration, and the methods for their introduction and elimination, are described in the literature and can be adapted where appropriate to the individual case without difficulties.

The present invention also relates to the use of compounds according to formula I as pharmaceutical or medicament.

The compounds of the general formula (I) are PARP inhibitors and are accordingly suitable for the treatment of diseases which are related to PARP, are promoted thereby or result from its involvement.

Examples of diseases which can be treated with the compounds according to the present invention include: tissue damage resulting from cell damage or cell death owing to necrosis or apoptosis, neuronally mediated tissue damage or disorders, cerebral ischemia, head trauma, stroke, reperfusion damage, neurological disturbances and neurodegenerative disorders, vascular stroke, cardiovascular disorders, myocardial infarction, myocardial ischemia, experimental allergic encephalomyelitis (EAE), multiple sclerosis (MS), ischemia related to heart surgery, age-related macular degeneration, arthritis, arteriosclerosis, cancer, degenerative disorders of the skeletal muscles with subsequent replicative senescence, diabetes and diabetic myocardial disorders.

The compounds of the present invention are preferably employed for the treatment of diseases which are caused by ischemia or reperfusion damage. Diseases which can be treated are more preferably selected from the group consisting of: cerebral ischemia, reperfusion damage, cardiovascular disorders, myocardial infarction, myocardial ischemia and ischemia related to heart surgery.

The compounds of the present invention can be used in particular for the treatment of a myocardial infarction.

The term treatment in the above statements also includes the prophylaxis, therapy or cure of the aforementioned diseases.

The compounds of the invention of the formula I and their physiologically tolerated salts can be used in animals, preferably in mammals, and in particular in humans as pharmaceutical on their own, mixed with one another or in the form of pharmaceutical preparations. The present invention also relates to the compounds of the formula I and their physiologically tolerated salts for use as pharmaceutical, their use in the therapy of said pathological stages and their use for the manufacture of medicaments therefor and of medicaments having a PARP-inhibiting effect. The present invention further relates to pharmaceutical preparations which comprise as active ingredient an effective dose of at least one compound of the formula I and/or of a physiologically tolerated salt thereof in addition to conventional, pharmaceutically acceptable carriers and excipients. The pharmaceutical preparations normally comprise from 0.1 to 90 percent by weight of the compounds of the formula I and/or of their physiologically tolerated salts. The pharmaceutical preparations can be manufactured in a manner known per se. For this purpose, the compounds of the formula I and/or their physiologically tolerated salts are mixed together with one or more solid or liquid pharmaceutical carriers and/or excipients and, if desired, converted in combination with other active pharmaceutical ingredients into a suitable presentation or dosage form which can then be used as pharmaceutical in human medicine or veterinary medicine.

Pharmaceuticals which comprise compounds of the invention of the formula I and/or their physiologically tolerated salts can be administered orally, parenterally, e.g. intravenously, rectally, by inhalation or topically, with the preferred administration being dependent on the individual case, e.g. the particular manifestation of the disorder to be treated.

The skilled worker is familiar on the basis of his expert knowledge with the excipients suitable for the desired pharmaceutical formulation. Besides solvents, gel formers, suppository bases, tablet excipients and other active ingredient carriers, it is possible to use for example antioxidants, dispersants, emulsifiers, antifoams, masking flavors, preservatives, solubilizers, agents to achieve a depot effect, buffer substances or colorants.

For a form for oral administration, the active compounds are mixed with the additives suitable for this purpose, such as carriers, stabilizers or inert diluents, and converted by conventional methods into suitable presentations such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for preparation to take place both as dry and as wet granules. Suitable oily carriers or solvents are for example vegetable or animal oils such as sunflower or fish liver oil. Suitable solvents for aqueous or alcoholic solutions are for example water, ethanol or sugar solutions or mixtures thereof. Further excipients, also for other administration forms, are for example polyethylene glycols and polypropylene glycols.

For subcutaneous or intravenous administration, the active compounds are converted if desired with the substances usual for this purpose, such as solubilizers, emulsifiers or further excipients, into solution, suspension or emulsion. The compounds of the formula I and their physiologically tolerated salts can also be lyophilized and the resulting lyophilizates be used for example for manufacturing products for injection or infusion. Examples of suitable solvents are water, physiologically saline or alcohols, e.g. ethanol, propanol, glycerol, as well as sugar solutions such as glucose or mannitol solutions, or else mixtures of the various solvents mentioned.

Pharmaceutical formulations suitable for administration in the form of aerosols or sprays are for example solutions, suspensions or emulsions of the active ingredients of the formula I or their physiologically tolerated salts in a pharmaceutically acceptable solvent such as, in particular, ethanol or water, or a mixture of such solvents. The formulation can if required also comprise other pharmaceutical excipients such as surfactants, emulsifiers and stabilizers, and a propellant gas. Such a preparation normally comprises the active ingredient in a concentration of about 0.1 to 10, in particular of about 0.3 to 3, percent by weight.

The dosage of the active ingredient of the formula I to be administered or of the physiologically tolerated salt thereof depends on the individual case and must be adapted as usual to the circumstances of the individual case for an optimal effect. It naturally depends on the frequency of administration and on the potency and duration of action of the respective compounds employed for the therapy or prophylaxis, but also on the nature and severity of the disease to be treated and on the gender, age, weight and individual response of the human or animal to be treated and on whether the therapy is acute or prophylactic. The daily dose of a compound of the formula I on administration to a patient weighing about 75 kg is normally 0.001 mg/kg of body weight to 100 mg/kg of body weight, preferably 0.01 mg/kg of body weight to 20 mg/kg of body weight. The dose can be administered in the form of a single dose or be divided into a plurality of, e.g. two, three or four, single doses. Especially for the treatment of acute cases of myocardial infarction, for example in an intensive care unit, parenteral administration by injection or infusion, e.g. by continuous intravenous infusion, may also be advantageous.

EXPERIMENTAL SECTION

| List of abbreviations | |
|---|---|
| nBuLi | n-butyllithium |
| DMF | N,N-dimethylformamide |
| DMSO | dimethyl sulfoxide |
| eq. | mole equivalent |
| MeCN | acetonitrile |
| MeOH | methanol |
| NaOtBu | sodium tert-butanolate |
| NBS | N-bromosuccinimide |
| NEt3 | triethylamine |
| NIS | N-iodosuccinimide |
| PdCl2(pddf) | 1,1'-bis(diphenylphosphino)ferrocenepalladium(II) chloride |
| Pd2dba3 | tris(dibenzylideneacetone)dipalladium(0) |
| RT | room temperature |
| RP-HPLC | reverse phase high performance chromatography |
| (tBu)2Pbiphenyl | di(tert-butyl) biphenylphosphine |
| TFA | trifluoroacetic acid |
| THF | tetrahydrofuran |
| TMSCl | trimethylsilyl chloride |
| KI | potassium iodide |

Synthesis of Halides of the Formula II

The synthesis shown in scheme 1 is demonstrated by means of the bromide (R1 equal to ethyl, R2 equal to hydrogen and R3 equal to methyl):

3-Bromo-5-ethyl-6-methoxy-2-methylpyridine (Compound 1)

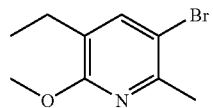

A mixture of 3-ethyl-6-methyl-1H-pyridin-2-one (23.92 g, 174.4 mmol) and N-bromosuccinimide (32.67 g, 183.5 mmol) in methanol (450 ml) was stirred under nitrogen at room temperature. A thick suspension formed after some hours and was stirred at RT for a further 24 h. The reaction mixture was concentrated to one half to one third of the original volume and diluted with 200 ml of water. The mixture was cooled in an ice bath with stirring and then filtered with suction. The residue was washed with cold water and dried at 65° C. 35.93 g (95%) of 5-bromo-3-ethyl-6-methyl-1H-pyridin-2-one were obtained in the form of a beige powder.

5-Bromo-3-ethyl-6-methyl-1H-pyridin-2-one (25 g, 115.7 mmol) was dissolved in 200 ml of chloroform to form an orange solution. Silver carbonate (31.9 g, 115.7 mmol) was added and the mixture was vigorously stirred. Methyl iodide (10.8 ml, 1.5 mmol) was added to this suspension, which was then stirred in the dark at RT under nitrogen. After 3 days, the mixture was filtered and the solution was concentrated in a rotary evaporator. The residue was chromatographed on silica gel with n-heptane as mobile phase and afforded a colorless oil (21.7 g, 82%).

MS: m/z=230 and 232 (M+1)

1H-NMR (CDCl3): δ=7.44 (s, 1H); 3.91 (s, 3H); 2.52 (q, 2H, J=7.6 Hz); 2.50 (s, 3H); 1.16 (t, 3H, J=7.6 Hz).

Synthesis of Boric Esters of the Formula III

The synthesis shown in scheme 1 is demonstrated by means of the pinacol ester of boric acid (R1 equal to ethyl, R2 equal to hydrogen and R3 equal to methyl):

3-Ethyl-2-methoxy-6-methyl-5-(4,4,5,5-tetramethyl-[1,3,2]dioxaborolan-2-yl)pyridine (Compound 2)

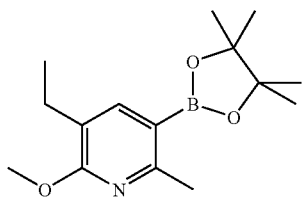

3-Bromo-5-ethyl-6-methoxy-2-methylpyridine (11.51 g, 50 mmol), 4,4,5,5-tetramethyl-1,3,2-dioxaborolane (8.31 g, 64.95 mmol) and triethylamine (21.84 ml, 164.4 mmol) were dissolved under argon in 100 ml of dioxane and then 1,1'bis(diphenylphosphino)ferrocenepalladium(II) chloride (1.94 g, 2.65 mmol) was added. The mixture was stirred at 90° C. for 18 h, cooled and diluted with ethyl acetate, and filtered through silica gel. The solution was cooled to 0° C., mixed with water and extracted twice with ethyl acetate. The dried and concentrated organic phase was chromatographed on silica gel dried at 45° C. in a vacuum drying oven. A pale beige solid (9.94 g, 72%) was obtained.

MS: m/z=278 (M+1)

1H-NMR (CDCl3): δ=7.68 (s, 1H); 3.95 (s, 3H); 2.62 (s, 3H); 2.53 (q, 2H, J=7.6 Hz); 1.33 (s, 12H); 1.16 (t, 3H, J=7.6 Hz).

Synthesis of Aniliopyridines of the Formula IV (Scheme 2)

General Procedure 135 mg (1.4 mmol) of sodium tert-butoxide were dissolved in 2 ml of toluene under argon, 230 mg (1 mmol) of compound 1 and 2 mmol of the respective aniline were added and stirred at RT for 10 min, and then 48 mg (0.16 mmol) of 2-(di-tert-butylphosphino)biphenyl and 9.2 mg (0.01 mmol) of tris(dibenzylideneacetone)palladium(0) were added. The mixture was reacted in a microwave (CEM Discover) at 100° C. for 30 min and then diluted with water and ethyl acetate and filtered through a kieselguhr cartridge (Varian Chem Elut). The desired product was isolated by RP-HPLC in yields of between 5 and 50%.

Synthetic Method for Compound 3

3-(5-Ethyl-6-methoxy-2-methylpyridin-3-ylamino)benzonitrile (Compound 3)

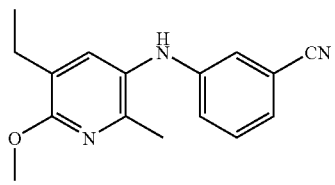

125 mg (1.3 mmol) of sodium tert-butoxide were dissolved in 2 ml of toluene under argon, 230 mg (1 mmol) of compound 1 and 236 mg (2 mmol) of 2-aminobenzonitrile were added and stirred at RT for 10 min, and then 48 mg (0.16 mmol) of 2-(di-tert-butylphosphino)biphenyl and 9.2 mg (0.01 mmol) of tris(dibenzylideneacetone)dipalladium(0) were added. The mixture was reacted in a microwave (CEM Discover) at 180° C. for 15 min, then diluted with water and ethyl acetate and extracted twice with ethyl acetate, and the organic phase was concentrated and then purified by RP-HPLC. 25 mg (9% of theory) of the title compound were obtained.

MS: m/z=268 (M+1)

The following compounds of the formula IV were prepared in accordance with the above general procedure. The anilines employed in this case for the compounds 4 to 21 and 24 to 30 were as follows:

4: 3-aminobenzamide; 5: 3-acetylaniline; 6: N-(3-aminophenyl)acetamide; 7: 3-aminoquinoline; 8: 4-aminobenzenesulfonamide; 9: 4-(pyridin-3-yloxy)aniline; 10: 4-(imidazol-1-yl)aniline; 11: 1-(6-amino-2,3-dihydroindol-1-yl)ethanone; 12: 4-amino-N-pyridin-2-ylbenzenesulfonamide; 13: 6-amino-3,4-dihydro-2H-naphthalen-1-one; 14: N-(6-aminopyridin-3-yl)acetamide; 15: 6-aminonicotinonitrile; 16: 5-aminoindan-1-one; 17: 4-aminopyridine; 18: 2-aminopyridine; 19: 2-acetylaniline; 20: 4-acetylaniline; 21: 3-aminopyridine; 24: 3-(methylaminomethyl)aniline; 25: 3-hydroxymethylaniline; 26: 3-methanesulfonylaniline; 27: 3-(2-methylpyrimidin-4-yl)aniline; 28: 3-pyrrolidin-1-ylmethylaniline; 29: 1-(3-aminophenyl)ethanol; 30: N-methylaniline.

| Compound | Structure | Mass m/z = |
|---|---|---|
| 4 | 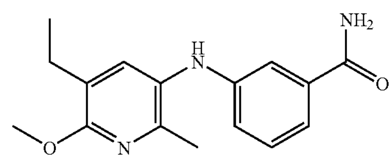 | 286 (M + 1) |
| 5 | 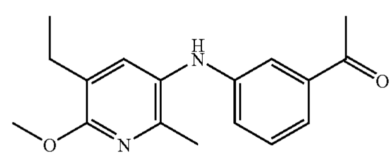 | 285 (M + 1) |
| 6 | 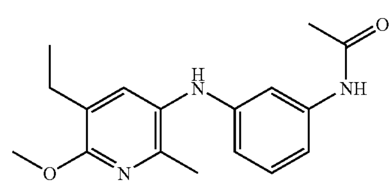 | 300 (M + 1) |
| 7 | 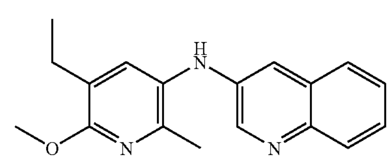 | 294 (M + 1) |
| 8 | 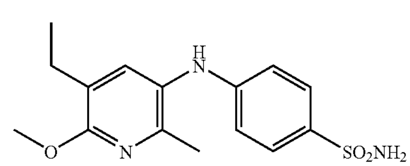 | 322 (M + 1) |

-continued

| Compound | Structure | Mass m/z = |
|---|---|---|
| 9 | 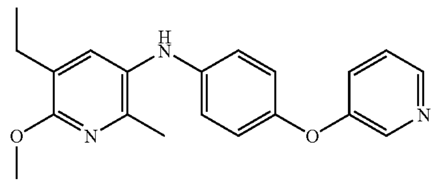 | 337 (M + 1) |
| 10 | 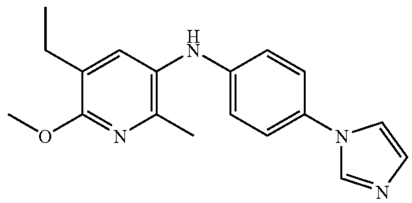 | 309 (M + 1) |
| 11 | 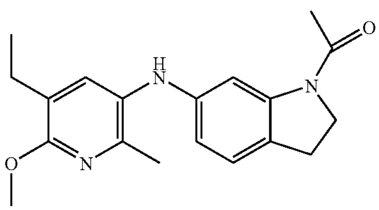 | 326 (M + 1) |
| 12 | 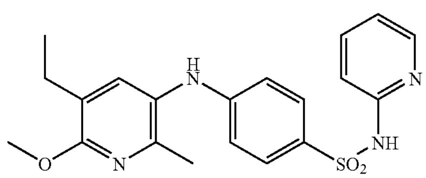 | 399 (M + 1) |
| 13 | 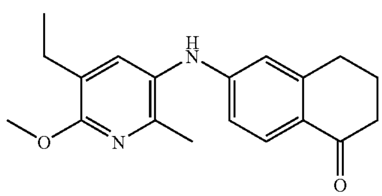 | 311 (M + 1) |
| 14 | 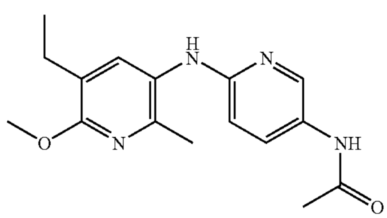 | 301 (M + 1) |
| 15 | 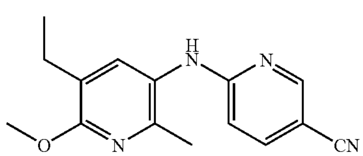 | 269 (M + 1) |
| 16 | 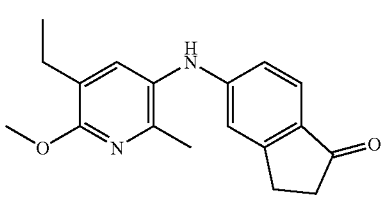 | 297 (M + 1) |

-continued

| Compound | Structure | Mass m/z = |
|---|---|---|
| 17 | 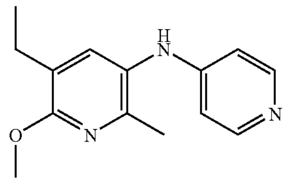 | 244 (M + 1) |
| 18 | 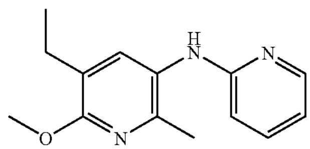 | 244 (M + 1) |
| 19 | 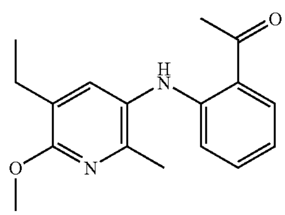 | 285 (M + 1) |
| 20 | 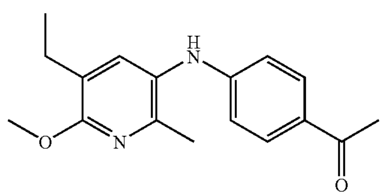 | 285 (M + 1) |
| 21 | 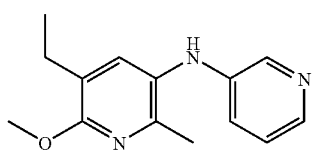 | 244 (M + 1) |
| 24 | 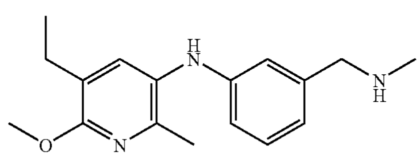 | 286 (M + 1) |
| 25 | 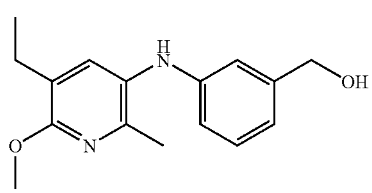 | 273 (M + 1) |
| 26 | 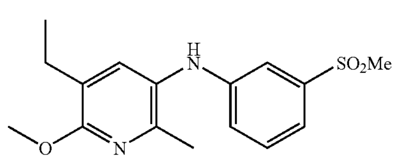 | 321 (M + 1) |

| Compound | Structure | Mass m/z = |
|---|---|---|
| 27 | 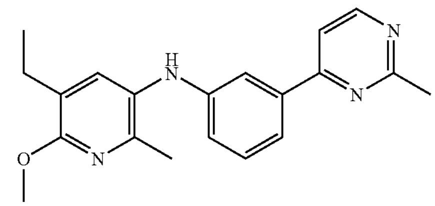 | 335 (M + 1) |
| 28 | 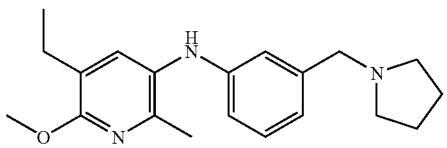 | 326 (M + 1) |
| 29 | 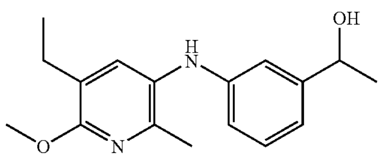 | 287 (M + 1) |
| 30 | 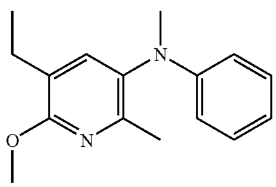 | 257 (M + 1) |

Synthesis of Aryl Ether Pyridines of the Formula V (Scheme 3)

3-Ethyl-2-methoxy-5-(3-methoxyphenoxy)-6-methylpyrindine (Compound 22)

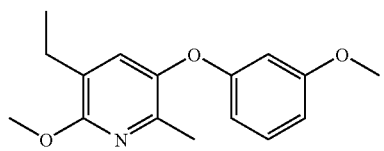

277 mg (1 mmol) of compound 2, 62 mg (0.5 mmol) of 3-methoxyphenol and 90 mg (0.5 mmol) of copper(II) acetate were mixed in 3 ml of dichloromethane, then 253 mg (2.5 mmol) of triethylamine were added, and the mixture was stirred at RT for 16 h. The mixture was mixed with water and dichloromethane, filtered through a kieselguhr cartridge and purified by RP-HPLC. 36 mg (26% of theory) of a colorless oil were obtained.

MS: m/z=274(M+1)

3-(5-Ethyl-6-methoxy-2-methylpyridin-3-yloxy)benzonitrile (Compound 23)

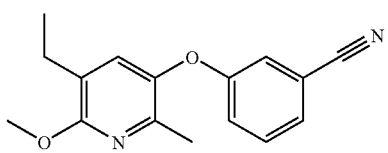

35 mg (26% of theory) of the abovementioned title compound were isolated analogously from 60 mg (0.5 mmol) of 3-cyanophenol.

MS: m/z=269 (M+1)

Synthesis of Pyridones of the Formula I by Deprotection of the 2-methoxypyridines of the Formula IV and V General Procedure 2 eq. of potassium iodide and 2 eq. of trimethylchlorosilane were added to a mixture of the 2-methoxypyridine of the formula V or V in anhydrous acetonitrile (3-5 ml/mmol) under argon, and the cloudy mixture was heated at 60-80° C. for 1-3 h. The mixture was then cooled to RT and diluted with water. The precipitated product was filtered off with suction, washed with water and dried in a vacuum drying oven at 40° C. The filtrate was extracted with ethyl acetate and occasionally afforded further product after concentration, which was purified—if necessary—by HPLC.

The following examples were synthesized in accordance with these methods:

| Example | Structure and compound name | Mass m/z = | NMR (CDCl$_3$) δ = |
|---|---|---|---|
| 1 | 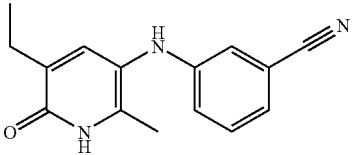<br>3-(5-Ethyl-2-methyl-6-oxo-1,6-dihydro-pyridin-3-ylamino)benzonitrile | 254 (M + 1) | |
| 2 | 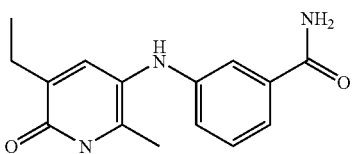<br>3-(5-Ethyl-2-methyl-6-oxo-1,6-dihydro-pyridin-3-ylamino)benzamide | 272 (M + 1) | |
| 3 | 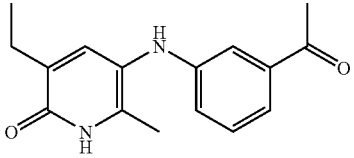<br>5-(3-Acetylphenylamino)-3-ethyl-6-methyl-1H-pyridin-2-one | 271 (M + 1) | 15.3(1H, br s), 7.59 (1H, s), 7.46(1H, m), 7.34(1H, m), 7.25(1H, m), 6.84(1H, m), 2.63 (2H, q, J=7.4Hz), 2.57 (3H, s), 2.43(3H, s), 1.20(3H, t, J=7.4Hz). |
| 4 | 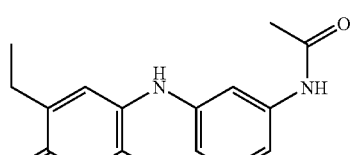<br>N-[3-(5-Ethyl-2-methyl-6-oxo-1,6-dihydro-pyridin-3-ylamino)phenyl]acetamide | 286 (M + 1) | 14.8(1H, br s), 7.59 (1H, s), 7.25(1H, m), 7.14(1H, m), 6.71(1H, m), 6.36(1H, m), 2.59 (2H, q, J=7.5Hz), 2.40 (3H, s), 2.15(3H, s), 1.19(3H, t, J=7.5Hz). |
| 5 | 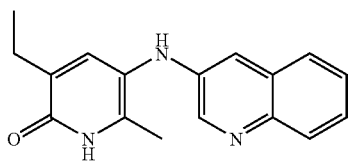<br>3-Ethyl-6-methyl-5-(quinolin-3-ylamino)-1H-pyridin-2-one | 280 (M + 1) | |
| 6 | 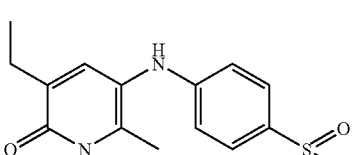<br>4-(5-Ethyl-2-methyl-6-oxo-1,6-dihydro-pyridin-3-ylamino)benzenesulfonamide | 308 (M + 1) | |

| Example | Structure and compound name | Mass m/z = | NMR (CDCl₃) δ = |
|---|---|---|---|
| 7 | 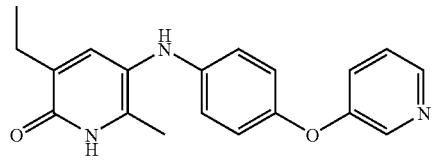<br>3-Ethyl-6-methyl-5-[4-(pyridin-3-yloxy)-phenylamino)-1H-pyridin-2-one | 323 (M + 1) | |
| 8 | 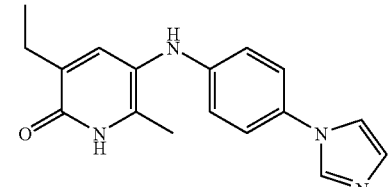<br>3-Ethyl-5-(4-imidazol-1-ylphenylamino)-6-methyl-1H-pyridin-2-one | 295 (M + 1) | |
| 9 | 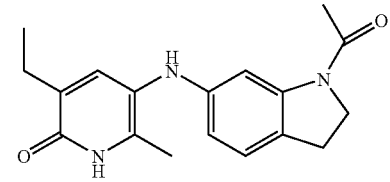<br>5-(1-Acetyl-2,3-dihydro-1H-indol-6-yl-amino)-3-ethyl-6-methyl-1H-pyridin-2-one | 312 (M + 1) | |
| 10 | 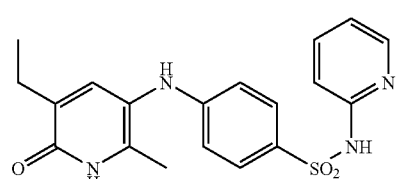<br>4-(5-Ethyl-2-methyl-6-oxo-1,6-dihydro-pyridin-3-ylamino)-N-pyridin-2-ylbenzene-sulfonamide | 385 (M + 1) | |
| 11 | 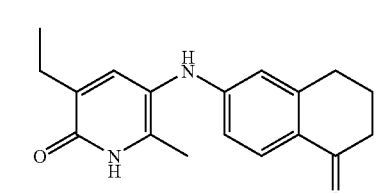<br>3-Ethyl-6-methyl-5-(5-oxo-5,6,7,8-tetra-hydronaphthalen-2-ylamino)-1H-pyridin-2-one | 297 (M + 1) | |
| 12 | 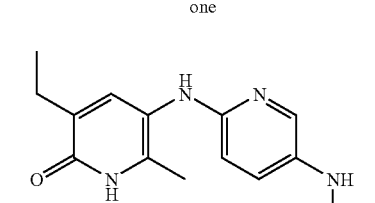<br>N-[6-(5-Ethyl-2-methyl-6-oxo-1,6-dihydro-pyridin-3-ylamino)pyridin-3-yl]acetamide | 287 (M + 1) | |

-continued

| Example | Structure and compound name | Mass m/z = | NMR (CDCl₃) δ = |
|---|---|---|---|
| 13 | 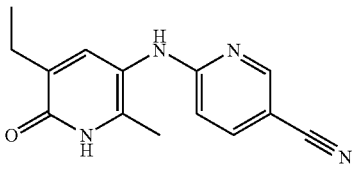<br>6-(5-Ethyl-2-methyl-6-oxo-1,6-dihydro-pyridin-3-ylamino)nicotinonitrile | 255 (M + 1) | |
| 14 | 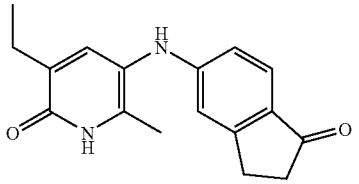<br>3-Ethyl-6-methyl-5-(1-oxoindan-5-ylamino)-1H-pyridin-2-one | 283 (M + 1) | |
| 15 | 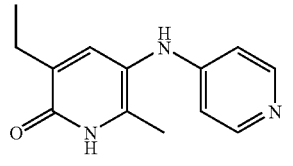<br>3-Ethyl-6-methyl-5-(pyridin-4-ylamino)-1H-pyridin-2-one | 230 (M + 1) | |
| 16 | 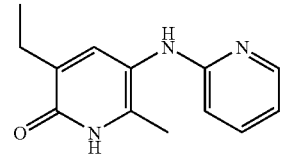<br>3-Ethyl-6-methyl-5-(pyridin-2-ylamino)-1H-pyridin-2-one | 230 (M + 1) | |
| 17 | 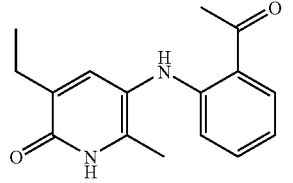<br>5-(2-Acetylphenylamino)-3-ethyl-6-methyl-1H-pyridin-2-one | 271 (M + 1) | |
| 18 | 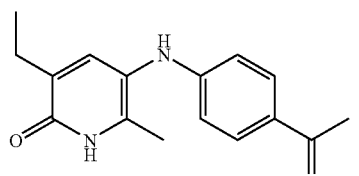<br>5-(4-Acetylphenylamino)-3-ethyl-6-methyl-1H-pyridin-2-one | 271 (M + 1) | |

-continued

| Example | Structure and compound name | Mass m/z = | NMR (CDCl$_3$) δ = |
|---|---|---|---|
| 19 | 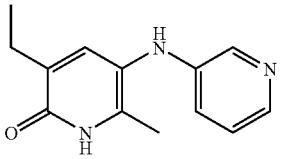<br>3-Ethyl-6-methyl-5-(pyridin-3-ylamino)-1H-pyridin-2-one | 230 (M + 1) | |
| 20 | 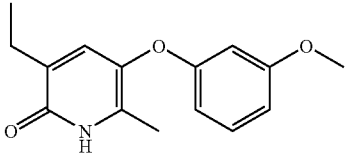<br>3-Ethyl-5-(3-methoxyphenoxy)-6-methyl-1H-pyridin-2-one | 260 (M + 1) | 11.7(1H, s), 7.21(1H, m), 7.08(1H, s), 6.61 (1H, m), 6.44(1H, m) 6.39(1H, m), 3.72(3H, s), 2.35(2H, q, J= 7.5Hz), 2.01(3H, s), 1.05(3H, t, J=7.5Hz). |
| 21 | 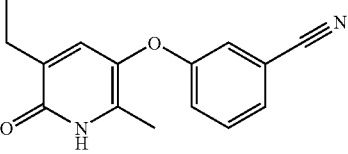<br>3-(5-Ethyl-2-methyl-6-oxo-1,6-dihydro-pyridin-3-yloxy)benzonitrile | 255 (M + 1) | |
| 22 | 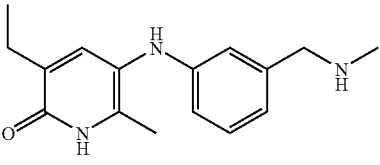<br>3-Ethyl-6-methyl-5-(3-methylaminomethyl-phenylamino)-1H-pyridin-2-one | 272 (M + 1) | |
| 23 | 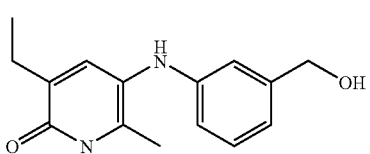<br>3-Ethyl-5-(3-hydroxymethylphenylamino)-6-methyl-1H-pyridin-2-one | 259 (M + 1) | |
| 24 | 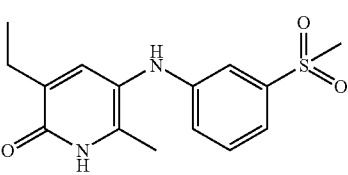<br>3-Ethyl-5-(3-methanesulfonylphenyl-amino)-6-methyl-1H-pyridin-2-one | 307 (M + 1) | |

-continued

| Example | Structure and compound name | Mass m/z = | NMR (CDCl₃) δ = |
|---|---|---|---|
| 25 | 3-Ethyl-6-methyl-5-[3-(2-methylpyrimidin-4-yl)phenylamino]-1H-pyridin-2-one | 321 (M + 1) | |
| 26 | 3-Ethyl-6-methyl-5-(3-pyrrolidin-1-yl-methylphenylamino)-1H-pyridin-2-one | 312 (M + 1) | |
| 27 | 3-Ethyl-5-[3-(1-hydroxyethyl)phenyl-amino]-6-methyl-1H-pyridin-2-one | 273 (M + 1) | |
| 28 | 3-Ethyl-6-methyl-5-(methylphenyl-amino)-1H-pyridin-2-one | 243 (M + 1) | |

Pharmacological Investigations

PARP Enzyme Assay

The half-maximum inhibitor concentration is determined by incubating the substances to be tested with the DNA-activated, recombinantly expressed and purified PARP-1 enzyme. Specifically, various concentrations of the test substance are incubated in 50 μl of reaction solution, which contains 50 mM Tris, 5 mM MgCl$_2$, 1 mM DTT, 200 μM NAD, 0.1 mCi/ml tritium-labeled NAD, 0.1 mg/ml DNA, 0.1 mg/ml histones, 2 μg/ml recombinantly expressed human PARP-1 enzyme, pH=8.0, at room temperature for 1 hour. The reaction is stopped by adding 150 μl of 20% trichloroacetic acid, and the radiolabelled protein constituents are precipitated. After incubation on ice for 10 minutes, the labeled, insoluble constituents are separated off through a glass fiber filter and, after washing with 20% trichloroacetic acid three times, the radioactivity incorporated by the PARP-1 enzyme is measured by radioluminescence. Consideration of the incorporation rates determined in this way as a function of the concentration of the test substance results in the half-maximum inhibitor concentration (IC$_{50}$) as the concentration of the test substance which reduces the incorporation rate to half the maximum value attainable (incubation without inhibitor).

The following IC-50 values were determined in this way for the compounds listed below:

| Ex. | IC-50 [μM] |
|---|---|
| 1 | 9.0 |
| 2 | 2.2 |
| 3 | 1.3 |
| 4 | 0.8 |
| 6 | 9.8 |
| 7 | 4.7 |
| 9 | 3.4 |
| 10 | 6.2 |
| 12 | 1.1 |
| 13 | 3.9 |
| 15 | 9.5 |
| 18 | 4.4 |
| 19 | 9.2 |
| 20 | 4.8 |
| 23 | 9.8 |
| 24 | 6.1 |

What is claimed is:

1. A compound of formula (I)

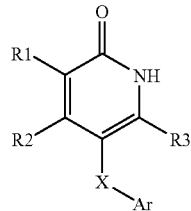

in which the meanings are:

R1 and R3 are, independently of one another,
fluorine, methoxy, —OCF$_3$, C$_2$-C$_3$-alkenyl or C$_1$-C$_4$-alkyl which is optionally substituted by chlorine, methoxy or one, two or three fluorine atoms;

R2 is hydrogen, fluorine, methoxy, —OCF$_3$, C$_2$-C$_3$-alkenyl or C$_1$-C$_4$-alkyl which is optionally substituted by chlorine, methoxy or one, two or three fluorine atoms;

X is O, S, NH or N(C$_1$-C$_3$-alkyl);

Ar is an unsubstituted or at least monosubstituted aryl or heteroaryl, where the substituents are selected from the group consisting of:
fluorine, chlorine, bromine, —CF$_3$, —OCF$_3$, —NO$_2$, —CN, —C(O)(C$_1$-C$_6$-alkyl), NH$_2$, —NHC(O)(C$_1$-C$_6$-alkyl), hydroxy, oxo, C$_1$-C$_6$-alkyl, C$_1$-C$_6$-alkoxy, —NH(C$_1$-C$_6$-alkyl), —N(C$_1$-C$_6$-alkyl)$_2$, —SO$_2$(C$_1$-C$_6$-alkyl), heterocyclyl, heteroaryl, aryl, —O-aryl, —O-heteroaryl, —CH$_2$—NR4R5, —SO$_2$NR4R5, and —C(O)NR4R5,
where the C$_1$-C$_6$-alkyl substituent may be substituted at least once by C$_1$-C$_6$-alkoxy, fluorine, chlorine, trifluoromethyl, trifluoromethoxy, aryl, heteroaryl, heterocyclyl or OH,
and the aryl, heteroaryl and heterocyclyl substituents may be substituted at least once by C$_1$-C$_6$-alkyl, C$_1$-C$_6$-alkoxy, fluorine, chlorine, trifluoromethyl, trifluoromethoxy or OH;

R4 and R5 are, independently of one another, selected from the group consisting of:
hydrogen; unsubstituted or at least monosubstituted C$_1$-C$_{10}$-alkyl, C$_2$-C$_6$-alkenyl, phenyl, indanyl, heterocyclyl and heteroaryl,
where the substituents are selected from the group consisting of:
phenyl, heteroaryl, heterocyclyl, —O-phenyl, fluorine, —CN, —C(O)NH$_2$, —C(O)(C$_1$-C$_3$-alkyl), —C(O)-phenyl, —N(C$_1$-C$_3$-alkyl)$_2$, —NH(C$_1$-C$_3$-alkyl), —NH$_2$, —NH-heteroaryl, —NH—C(O)-heteroaryl, C$_1$-C$_6$-alkyl, C$_1$-C$_3$-alkoxy and hydroxy,
and the phenyl, heterocyclyl and heteroaryl fragments of these substituents may in turn be at least monosubstituted by fluorine, chlorine, bromine, oxo, —CF$_3$, —OCF$_3$, —NO$_2$, —CN, phenyl, pyridinyl, —NHC(O)(C$_1$-C$_3$-alkyl), —COOH, hydroxy, C$_1$-C$_3$-alkyl, C$_1$-C$_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or —N(C$_1$-C$_3$-alkyl)$_2$; or R4 and R5 form, together with the nitrogen atom to which they are bonded, unsubstituted or at least monosubstituted heterocyclyl,
where the substituents are selected from the group consisting of:
phenyl, heteroaryl, heterocyclyl, oxo, fluorine, chlorine, —C(O)(C$_1$-C$_3$-alkyl), —C(O)-phenyl and hydroxy,
and the phenyl, heterocyclyl and heteroaryl fragments of these substituents may in turn be at least monosubstituted by fluorine or C$_1$-C$_3$-alkyl;

wherein at all occurrences herein;
aryl is a 5 to 10-membered aromatic mono- or bicycle;
heteroaryl is a 5 to 10-membered aromatic mono- or bicyclic heterocycle which comprises one or more heteroatoms selected from N, O and S; and
heterocyclyl is a 5 to 10-membered nonaromatic mono- or bicyclic heterocycle which comprises one or more heteroatoms selected from N, O and S;
or a physiologically tolerated salt thereof;
with the proviso that Ar is not triazinyl or chromanyl, and Ar is not pyridopyrazinyl or naphthyridinyl when X is NH or N(C$_1$-C$_3$-alkyl).

2. A compound as claimed in claim 1, in which the meanings are:

X is O, NH or N(C$_1$-C$_3$-alkyl);
R1 is fluorine, —OCF$_3$ or C$_1$-C$_4$-alkyl;
R2 is hydrogen, fluorine, —OCF$_3$ or C$_1$-C$_4$-alkyl;
R3 is fluorine, —OCF$_3$ or C$_1$-C$_4$-alkyl;
Ar is an unsubstituted or monosubstituted phenyl or heteroaryl, where the substituents are selected from the group consisting of:
fluorine, chlorine, —CF$_3$, —OCF$_3$, —CN, —C(O)(C$_1$-C$_3$-alkyl), NH$_2$, —NHC(O)(C$_1$-C$_3$-alkyl), hydroxy, oxo, C$_1$-C$_3$-alkyl, C$_1$-C$_3$-alkoxy, —NH(C$_1$-C$_3$-alkyl), —N(C$_1$-C$_3$-alkyl)$_2$, —SO$_2$(C$_1$-C$_3$-alkyl), heterocyclyl, heteroaryl, aryl, —O-aryl, —O-heteroaryl, —CH$_2$—NR4R5, —SO$_2$—NR4R5, and —C(O)NR4R5,
where the C$_1$-C$_3$-alkyl substituent may be at least monosubstituted by C$_1$-C$_3$-alkoxy, fluorine, chlorine, trifluoromethyl, trifluoromethoxy, aryl, heteroaryl, heterocyclyl or OH,
and the aryl, heteroaryl and heterocyclyl substituents may be at least monosubstituted by C$_1$-C$_3$-alkyl, C$_1$-C$_3$-alkoxy, fluorine, chlorine, trifluoromethyl, trifluoromethoxy or OH;

R4 is hydrogen or C$_1$-C$_3$-alkyl;
R5 is selected from the group consisting of; hydrogen; unsubstituted or at least monosubstituted C$_1$-C$_6$-alkyl, cyclohexenyl, indanyl, phenyl, pyrrolidinyl, pyrrolyl, pyrazolyl, furanyl and piperidinyl,
where the substituents are selected from the group consisting of: fluorine, —CN, —C(O)NH$_2$, —O-phenyl, —C(O)-phenyl, —N(CH$_3$)$_2$, C$_1$-C$_3$-alkyl, C$_1$-C$_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, whose substituents are in turn selected from the group consisting of: fluorine, chlorine, oxo, CF$_3$, —OCF$_3$, —NO$_2$, phenyl, pyridinyl, —NHC(O)CH$_3$, —COOH, hydroxy, C$_1$-C$_3$-alkyl, C$_1$-C$_3$-alkoxy, —SO$_2$NH$_2$, —C(O)NH$_2$ and —N(CH$_3$)$_2$; or R4 and R5 form, together with the nitrogen atom to which they are bonded, a radical selected from the group consisting of: unsubstituted or at least monosubstituted piperidinyl, pyrrolidinyl, morpholinyl and piperazinyl, where the substituents are selected from the group consisting of: fluorine, —C(O)(C$_1$-C$_3$-alkyl), oxo, C$_1$-C$_3$-alkyl, hydroxy, unsubstituted or at least monosubstituted phenyl, imidazolyl, pyridinyl, pyrimidinyl, piperidinyl and pyrrolidinyl, whose substituents are in turn fluorine or C$_1$-C$_3$-alkyl;

wherein at all occurrences herein:

aryl is phenyl, indanyl or naphthyl;

heteroaryl is pyridinyl, thienyl, pyrimidinyl, imidazolyl, furanyl, indolyl, benzimidazolyl, pyrazolyl, 1,3-benzodioxolyl, triazolyl, thiazolyl, isoxazolyl, pyrrolyl, pyrazinyl, oxazolyl, pyridazinyl, quinolinyl, isoquinolinyl, benzofuranyl, 3-oxo-1,3-dihydroisobenzofuranyl, 2,3-dihydroindolyl or 4,5,6,7-tetrahydrobenzothiazolyl; and heterocyclyl is morpholinyl, pyrrolidinyl, piperidinyl, tetrahydropyranyl, thiazolidinyl, dihydroisoxazolyl, piperazinyl or tetrahydrofuranyl;

or a physiologically tolerated salt thereof.

3. A compound as claimed in claim 1, in which the meanings are:

X is NH or N(C$_1$-C$_3$-alkyl);

R1 is C$_1$-C$_3$-alkyl;

R2 is hydrogen;

R3 is C$_1$-C$_3$-alkyl;

Ar is an unsubstituted or monosubstituted phenyl, indolyl, benzofuranyl, benzimidazolyl, furanyl, thienyl, imidazolyl, pyrimidinyl, pyrazolyl, isoquinolinyl, pyridinyl, quinolinyl, or 2,3-dihydroindolyl, where the substituents are selected from the group consisting of:

fluorine, chlorine, —CF$_3$, —OCF$_3$, —CN, —C(O)(C$_1$-C$_3$-alkyl), NH$_2$, —NHC(O)(C$_1$-C$_3$-alkyl), hydroxy, oxo, C$_1$-C$_3$-alkyl, C$_1$-C$_3$-alkoxy, —NH(C$_1$-C$_3$-alkyl), —N(C$_1$-C$_3$-alkyl)$_2$, —SO$_2$(C$_1$-C$_3$-alkyl), heteroaryl, phenyl, —O-phenyl, —O-heteroaryl, —CH$_2$—NR4R5, —SO$_2$—NR4R5, and —C(O)NR4R5, where the C$_1$-C$_3$-alkyl substituent may be at least monosubstituted by C$_1$-C$_3$-alkoxy, fluorine, chlorine, trifluoromethyl, trifluoromethoxy, phenyl, heteroaryl or OH, and the phenyl and heteroaryl substituents may be at least monosubstituted by C$_1$-C$_3$-alkyl, C$_1$-C$_3$-alkoxy, fluorine, chlorine, trifluoromethyl, trifluoromethoxy or OH;

R4 is hydrogen

R5 is selected from the group consisting of hydrogen; unsubstituted or monosubstituted C$_1$-C$_6$-alkyl, cyclohexenyl, indanyl, phenyl, pyrrolidinyl, pyrrolyl, pyrazolyl, furanyl and piperidinyl, where the substituents are selected from the group consisting of: fluorine, —CN, —C(O)NH$_2$, —O-phenyl, —C(O)-phenyl, —N(CH$_3$)$_2$, C$_1$-C$_3$-alkyl, C$_1$-C$_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, whose substituents are in turn selected from the group consisting of: fluorine, chlorine, oxo, CF$_3$, —OCF$_3$, —NO$_2$, phenyl, pyridinyl, —NHC(O)CH$_3$, —COOH, hydroxy, C$_1$-C$_3$-alkyl, C$_1$-C$_3$-alkoxy, —SO$_2$NH$_2$, —C(O)NH$_2$ and —N(CH$_3$)$_2$; or R4 and R5 form together with the nitrogen atom to which they are bonded an unsubstituted or at least monosubstituted pyrrolidinyl radical, where the substituents are selected from the group consisting of: C$_1$-C$_3$-alkyl and hydroxy;

wherein at all occurrences herein:

heteroaryl is pyridinyl, quinolinyl, indolyl, benzofuranyl, thienyl, pyrimidinyl, imidazolyl, furanyl, benzimidazolyl, pyrazolyl, thiazolyl, isoquinolinyl, pyrrolyl or 2,3-dihydroindolyl;

or a physiologically tolerated salt thereof.

4. A compound as claimed in claim 1, in which the meanings are:

X is NH or N-methyl;

R1 is ethyl;

R2 is hydrogen;

R3 is methyl;

Ar is an unsubstituted or monosubstituted phenyl, indanyl, 5,6,7,8-tetra-hydronaphthyl, pyridinyl, quinolinyl, or 2,3-dihydroindolyl, where the substituents are selected from the group consisting of: —CN, —C(O)(C$_1$-C$_3$-alkyl), —NHC(O)(C$_1$-C$_3$-alkyl), oxo, C$_1$-C$_3$-alkyl, C$_1$-C$_3$-alkoxy, —SO$_2$(C$_1$-C$_3$-alkyl), heteroaryl, —O-heteroaryl, —CH$_2$—NR4R5, —SO$_2$—NR4R5, and —C(O)NR4R5, where the C$_1$-C$_3$-alkyl substituent may be monosubstituted by heteroaryl or OH, and the heteroaryl substituent may be monosubstituted by C$_1$-C$_3$-alkyl;

R4 is hydrogen

R5 is hydrogen, C$_1$-C$_3$-alkyl) or pyridinyl;

R4 and R5 form together with the nitrogen atom to which they are bonded a pyrrolidinyl radical;

wherein at all occurrences herein:

heteroaryl is pyridinyl, imidazolyl, or pyrimidinyl;

or a physiologically tolerated salt thereof.

5. A compound as claimed in claim 1 selected from the group consisting of:

3-(5-ethyl-2-methyl-6-oxo-1,6-dihydropyridin-3-ylamino)benzonitrile;

3-(5-ethyl-2-methyl-6-oxo-1,6-dihydropyridin-3-ylamino)benzamide;

5-(3-acetylphenylamino)-3-ethyl-6-methyl-1H-pyridin-2-one;

N-[3-(5-ethyl-2-methyl-6-oxo-1,6-dihydropyridin-3-ylamino)phenyl]acetamide;

3-ethyl-6-methyl-5-(quinolin-3-ylamino)-1H-pyridin-2-one;

4-(5-ethyl-2-methyl-6-oxo-1,6-dihydropyridin-3-ylamino)benzenesulfonamide;

3-ethyl-6-methyl-5-[4-(pyridin-3-yloxy)phenylamino]-1H-pyridin-2-one;

3-ethyl-5-(4-imidazol-1-ylphenylamino)-6-methyl-1H-pyridin-2-one;

5-(1-acetyl-2,3-dihydro-1H-indol-6-ylamino)-3-ethyl-6-methyl-1H-pyridin-2-one;

4-(5-ethyl-2-methyl-6-oxo-1,6-dihydropyridin-3-ylamino)-N-pyridin-2-yl-benzenesulfonamide;

3-ethyl-6-methyl-5-(5-oxo-5,6,7,8-tetrahydronaphthalen-2-ylamino)-1H-pyridin-2-one;

N-[6-(5-ethyl-2-methyl-6-oxo-1,6-dihydropyridin-3-ylamino)pyridin-3-yl]-acetamide;

6-(5-ethyl-2-methyl-6-oxo-1,6-dihydropyridin-3-ylamino)nicotinonitrile;

3-ethyl-6-methyl-5-(1-oxoindan-5-ylamino)-1H-pyridin-2-one;

3-ethyl-6-methyl-5-(pyridin-4-ylamino)-1H-pyridin-2-one;

3-ethyl-6-methyl-5-(pyridin-2-ylamino)-1H-pyridin-2-one;

5-(2-acetylphenylamino)-3-ethyl-6-methyl-1H-pyridin-2-one;

5-(4-acetylphenylamino)-3-ethyl-6-methyl-1H-pyridin-2-one;

3-ethyl-6-methyl-5-(pyridin-3-ylamino)-1H-pyridin-2-one;

3-ethyl-5-(3-methoxyphenoxy)-6-methyl-1H-pyridin-2-one;

3-(5-ethyl-2-methyl-6-oxo-1,6-dihydropyridin-3-yloxy)benzonitrile;

3-ethyl-6-methyl-5-(3-methylaminomethylphenylamino)-1H-pyridin-2-one;

3-ethyl-5-(3-hydroxymethylphenylamino)-6-methyl-1H-pyridin-2-one;

3-ethyl-5-(3-methanesulfonylphenylamino)-6-methyl-1H-pyridin-2-one;

3-ethyl-6-methyl-5-[3-(2-methylpyrimidin-4-yl)phenylamino]-1H-pyridin-2-one;

3-ethyl-6-methyl-5-(3-pyrrolidin-1-ylmethylphenylamino)-1H-pyridin-2-one;

3-ethyl-5-[3-(1-hydroxyethyl)phenylamino]-6-methyl-1H-pyridin-2-one;

3-ethyl-6-methyl-5-(methylphenylamino)-1H-pyridin-2-one;

or a physiologically tolerated salt thereof.

6. A method for the treatment of a patient suffering from, or subject to, a disease which can be ameliorated by the administration of a PARP inhibitor comprising administering to said patient an effective amount of a compound according to claim 1, wherein the disease is selected from the group consisting of: cerebral ischemia, reperfusion damage, cardiovascular disorders, myocardial infarction, myocardial ischemia and ischemia related to heart surgery.

7. The method as claimed in claim 6, wherein the disease is myocardial infarction.

8. A pharmaceutical composition comprising an effective amount of at least one compound as claimed in claim 1 and a physiologically acceptable carrier.

* * * * *

UNITED STATES PATENT AND TRADEMARK OFFICE
CERTIFICATE OF CORRECTION

PATENT NO.        : 7,863,280 B2
APPLICATION NO.   : 11/733833
DATED             : January 4, 2011
INVENTOR(S)       : Stefan Peukert et al.

It is certified that error appears in the above-identified patent and that said Letters Patent is hereby corrected as shown below:

In column 1, line 15, delete "apoptosis" and insert -- apoptosis. --, therefor.

In column 13, line 30, delete "$C_1$-$C_3$-alkyl)" and insert -- ($C_1$-$C_3$-alkyl) --, therefor.

In column 27, line 47-48, delete "methylpyrindine" and insert -- methylpyridine --, therefor.

In column 42, line 30, in claim 4, delete "$C_1$-$C_3$-alkyl)" and insert -- ($C_1$-$C_3$-alkyl) --, therefor.

Signed and Sealed this
Twenty-first Day of June, 2011

David J. Kappos
*Director of the United States Patent and Trademark Office*